(12) United States Patent
Granoff et al.

(10) Patent No.: US 8,476,032 B2
(45) Date of Patent: Jul. 2, 2013

(54) **COMPLEMENT FACTOR H-BASED ASSAYS FOR SERUM BACTERICIDAL ACTIVITY AGAINST *NEISSERIA MENINGITIDIS***

(75) Inventors: Dan M. Granoff, Berkeley, CA (US); JoAnne Welsch, Emeryville, CA (US); Sanjay Ram, Worcester, MA (US)

(73) Assignees: Children's Hospital & Research Center Oakland, Oakland, CA (US); Novartis Vaccines and Diagnostics, SRL, Siena (IT); The University of Massachusetts, Boston, MA (US)

( * ) Notice: Subject to any disclaimer, the term of this patent is extended or adjusted under 35 U.S.C. 154(b) by 482 days.

(21) Appl. No.: 12/548,316

(22) Filed: Aug. 26, 2009

(65) Prior Publication Data

US 2010/0240075 A1 Sep. 23, 2010

Related U.S. Application Data

(60) Provisional application No. 61/092,356, filed on Aug. 27, 2008.

(51) Int. Cl.
*G01N 33/554* (2006.01)
*G01N 33/53* (2006.01)

(52) U.S. Cl.
USPC .............................. 435/7.32; 435/7.2; 435/7.1

(58) Field of Classification Search
None
See application file for complete search history.

(56) References Cited

PUBLICATIONS

Ala'Aldeen, D. A. et al. (2000) "Dynamics of meningococcal long-term carriage among university students and their implications for mass vaccination" *J Clin Microbiol* 38(6):2311-2316.
Andrews, N et al. (2003) "Validation of serological correlate of protection for meningococcal C conjugate vaccine by using efficacy estimates from postlicensure surveillance in England" *Clin Diagn Lab Immunol* 10(5):780-786.
Ashton, F. E. et al. (1989) "Protective efficacy of mouse serum to the N-propionyl derivative of meningococcal group B polysaccharide" *Microb Pathog* 6(6):455-458.
Balmer & Borrow (2004) "Serologic correlates of protection for evaluating the response to meningococcal vaccines" *Expert Rev Vaccines* 3(1):77-87.
Bogaert, D. et al. (2005) "Epidemiology of nasopharyngeal carriage of *Neisseria meningitidis* in healthy Dutch children" *Clin Infect Dis* 40(6):899-902.
Borrow, R. et al. (2001) "Serological basis for use of meningococcal serogroup C conjugate vaccines in the United Kingdom: reevaluation of correlates of protection" *Infect Immun* 69(3):1568-1573.
Borrow, R. et al. (2005) "Meningococcal surrogates of protection—serum bactericidal antibody activity" *Vaccine* 23(17-18):2222-2227.
Fischer, et al. (1999) "*Neisseria meningitidis* serogroup B outer membrane vesicle vaccine in adults with occupational risk for meningococcal disease" *Vaccine* 17(19):2377-2383.

Fletcher et al. (2004) "Vaccine potential of the *Neisseria meningitidis* 2086 lipoprotein" *Infect. Immun.* 72(4):2088-2100.
GenBank Accession No. EU888587 "Ovis aries complement factor H (CFH) mRNA, partial cds" dated Aug. 18, 2008.
GenBank Accession No. NM_000186 "*Homo sapiens* complement factor H (CFH), nuclear gene encoding mitochondrial protein, transcript variant 1, mRNA" dated Aug. 24, 2008.
GenBank Accession No. NM_001014975 "*Homo sapiens* complement factor H (CFH), nuclear gene encoding mitochondrial protein, transcript variant 2, mRNA" dated Aug. 24, 2008.
GenBank Accession No. NM_009888 "*Mus musculus* complement component factor h (CfH), nuclear gene encoding mitochondrial protein, mRNA" dated Feb. 11, 2008.
Goldschneider et al. (1969) "Human immunity to the meningococcus. I. The role of humoral antibodies" *J. Exp. Med.* 129(6):1307-1326.
Goldschneider, et al. (1969) "Human immunity to the meningococcus. I. Development of natural immunity" *J Exp Med* 129(6):1327-1348.
Granoff (2009) "Relative importance of complement-mediated bactericidal and opsonic activity for protection against meningococcal disease" *Vaccine* 27(Suppl. 2):B117-125. doi:10.1016/j.vaccine.2009.04.066.
Harris, S. L. et al. (2003) "Age-related disparity in functional activities of human group C serum anticapsular antibodies elicited by meningococcal polysaccharide vaccine" *Infect. Immun.* 71(1):275-286.
Holbein, et al. (1979) "*Neisseria meningitidis* infection in mice: influence of iron, variations in virulence among strains, and pathology" *Infect Immun.* 24(2):545-551.
Jodar, L. et al. (2000) "Standardisation and validation of serological assays for the evaluation of immune responses to *Neisseria meningitidis* serogroup A and C vaccines" *Biologicals* 28(3):193-197.
Maiden, et al. (2008) "Impact of meningococcal serogroup C conjugate vaccines on carriage and herd immunity" *J. Infect. Dis.* 197(5):737-743.
Mountzouros & Howell (2000) "Detection of Complement Mediated Antibody-Dependent Bactericidal activity in a Fluorescence-Based Serum Bactericidal Assay for Group B *Neisseria meningitidis*" *J. Clin. Microbiol.* 38(8):2878-2884.
Mueller, et al. (2007) "Molecular characteristics and epidemiology of meningococcal carriage, Burkina Faso, 2003" *Emerg. Infect. Dis.* 13(6):847-854.
Oster, et al. (2007) "Immunogenicity and safety of a strain-specific MenB OMV vaccine delivered to under 5-year olds in New Zealand" *Vaccine* 25(16):3075-3079.
Perkins, et al. (1998) "Immunogenicity of two efficacious outer membrane protein-based serogroup B meningococcal vaccines among young adults in Iceland" *J. Infect. Dis.* 177(3):683-691.

(Continued)

*Primary Examiner* — S. Devi
(74) *Attorney, Agent, or Firm* — Carol L. Francis; Bozicevic, Field & Francis LLP

(57) ABSTRACT

Assays for detection of bactericidal anti-Neisserial antibodies using a factor H polypeptide having a human amino acid sequence that mediates binding to Neisserial factor H binding protein (fHBp) are provided, as well as non-human animal models of Neisserial infection.

20 Claims, 9 Drawing Sheets

PUBLICATIONS

Sandbu, et al. (2007) "Immunogenicity and safety of a combination of two serogroup B meningococcal outer membrane vesicle vaccines" *Clin. Vaccine Immunol.* 14(9):1062-1069.

Tappero, et al. (1999) "Immunogenicity of 2 serogroup B outer-membrane protein meningococcal vaccines: a randomized controlled trial in Chile" *JAMA* 281(16):1520-1527.

Thomas & Dingle (1943) "Investigations of Meningococcal Infection. III. The Bactericidal Action of Normal and Immune Sera for the meningococcus" *J. Clin. Invest.* 22(3):375-385.

Thornton, et al. (2006) "Safety and immunogenicity of New Zealand strain meningococcal serogroup B OMV vaccine in healthy adults: beginning of epidemic control" *Vaccine* 24(9):1395-1400.

Toropainen, et al. (1999) "The infant rat model adapted to evaluate human sera for protective immunity to group B meningococci" *Vaccine* 17(20-21):2677-2689.

Toropainen, et al. (2001) "Murine monoclonal antibodies to PorA of *Neisseria meningitidis* show reduced protective activity in vivo against B:15:P1.7,16 subtype variants in an infant rat infection model" *Microb. Pathog.* 30(3):139-148.

Toropainen, et al. (2005) "Passive protection in the infant rat protection assay by sera taken before and after vaccination of teenagers with serogroup B meningococcal outer membrane vesicle vaccines" *Vaccine* 23(40):4821-4833.

Toropainen, et al. (2005) "Protection by natural human immunoglobulin M antibody to meningococcal serogroup B capsular polysaccharide in the infant rat protection assay is independent of complement-mediated bacterial lysis" *Infect. Immun.* 73(8):4694-4703.

Toropainen, et al. (2006) "Protection by meningococcal outer membrane protein PorA-specific antibodies and a serogroup B capsular polysaccharide-specific antibody in complement-sufficient and C6-deficient infant rats" *Infect. Immun.* 74(5):2803-2808.

Trotter, et al. (2006) "The natural history of meningococcal carriage and disease" *Epidemiol. Infect.* 134(3):556-566.

Verdú, et al. (2001) "Association between asymptomatic carriage and sporadic (endemic) meningococcal disease in an open community" *Epidemiol. Infect.* 127(2):245-259.

Wedege, E. et al. (2007) "Functional and specific antibody responses in adult volunteers in New Zealand who were given one of two different meningococcal serogroup B outer membrane vesicle vaccines" *Clin. Vaccine. Immunol.* 14(7):830-838.

Wong, et al. (2007) "New Zealand epidemic strain meningococcal B outer membrane vesicle vaccine in children aged 16-24 months" *Pediatr. Infect. Dis. J.* 26(4):345-350.

Beernink, et al., Bactericidal Antibody Responses Induced by Meningococcal Recombinant Chimeric Factor H-Binding Protein Vaccines, Infection and Immunity, Jun. 2008, p. 2568-2575, vol. 76, No. 6.

Maslanka, et al., Standardization and a multilaboratory comparison of *Neisseria meningitidis* serogroup A and C serum bactericidal assays. The Multilaboratory Study Group, Clinical and Diagnostic Laboratory Immunology, Mar. 1997, 156-167, vol. 4, No. 2.

Granoff et al., Binding of complement factor H (fH) to *Neisseria meningitidis* is specific for human fH and inhibits complement activation by rat and rabbit sera. Infect Immun 2009;77(2):764-9.

Granoff et al., Immunogenicity of an investigational quadrivalent *Neisseria meningitidis*-diphtheria toxoid conjugate vaccine in 2-year old children. Vaccine 2005;23(34):4307-14.

Granoff et al., Persistence of group C anticapsular antibodies two to three years after immunization with an investigational quadrivalent *Neisseria meningitidis*-diphtheria toxoid conjugate vaccine. Pediatr Infect Dis J 2005;24 (2):132-6.

Haralambous et al., Factor H, a regulator of complement activity, is a major determinant of meningococcal disease susceptibility in UK Caucasian patients. Scand J Infect Dis 2006;38(9):764-71.

Hou et al., Protective antibody responses elicited by a meningococcal outer membrane vesicle vaccine with overexpressed genome-derived neisserial antigen 1870. J Infect Dis 2005;192(4):580-90.

Jarva et al., *Streptococcus pneumoniae* evades complement attack and opsonophagocytosis by expressing the pspC locus-encoded Hic protein that binds to short consensus repeats 8-11 of factor H. J Immunol 2002;168 (4):1886-94.

Kraiczy et al., Complement escape of human pathogenic bacteria by acquisition of complement regulators. Mol Immunol 2006;43(1-2):31-44.

Madico et al., The meningococcal vaccine candidate GNA1870 binds the complement regulatory protein factor H and enhances serum resistance. J Immunol 2006;177(1):501-10.

Masignani et al., Vaccination against *Neisseria meningitidis* using three variants of the lipoprotein GNA1870. J Exp Med 2003;197(6):789-99.

Ngampasutadol et al, A Novel Interaction between Factor H SCR 6 and the meningococcal vaccine candidate GNA1870: Implications for meningococcal pathogenesis and vaccine development. Abstracts/Molecular Immunology 2007;44:165.

Ngampasutadol et al., Human factor H interacts selectively with *Neisseria gonorrhoeae* and results in species-specific complement evasion. J Immunol 2008;180(5):3426-35.

Oftung et al., A mouse model utilising human transferrin to study protection against *Neisseria meningitidis* serogroup B induced by outer membrane vesicle vaccination. FEMS Immunol Med Microbol 1999;26(1):75-82.

Plested et al., Vaccine-induced opsonophagocytic immunity to *Neisseria meningitidis* group B. Clin Vaccine Immunol 2008;15(5):799-804.

Ram et al., Binding of complement factor H to loop 5 of porin protein 1A: a molecular mechanism of serum resistance of nonsialylated *Neisseria gonorrhoeae*. J Exp Med 1998;188(4):671-80.

Santos et al., Importance of complement source in measuring meningococcal bactericidal titers. Clin Diagn Lab Immunol 2001;8(3):616-23.

Schneider et al., Functional significance of factor H binding to *Neisseria meningitidis*. J Immunol 2006;176 (12):7566-75.

Seib et al, Factor H-binding protein is important for meningococcal survival in human whole blood and serum and in the presence of the antimicrobial peptide LL-37. Infect Immun 2009;77(1):292-9.

Vu et al., Antibody persistence 3 years after immunization of adolescents with quadrivalent meningococcal conjugate vaccine. J Infect Dis 2006;193(6):821-8.

Welsch et al., Antibody to genome-derived neisserial antigen 2132, a *Neisseria meningitidis* candidate vaccine, confers protection against bacteremia in the absence of complement-mediated bactericidal activity. J Infect Dis 2003;188(11):1730-40.

Welsch et al., Complement-dependent synergistic bactericidal activity of antibodies against factor H-binding protein, a sparsely distributed meningococcal vaccine antigen. J Infect Dis 2008;197(7):1053-61.

Welsch et al., Immunity to *Neisseria meningitidis* group B in adults despite lack of serum bactericidal antibody. Clin Vaccine Immunol 2007;14(12)1596-1602.

Welsch et al., Naturally acquired passive protective activity against *Neisseria meningitidis* Group C in the absence of serum bactericidal activity. Infect Immun 2004;72(10):5903-9.

Welsch et al., Protective activity of monoclonal antibodies to genome-derived neisserial antigen 1870, a *Neisseria meningitidis* candidate vaccine. J Immunol 2004;172(9):5606-15.

Zarantonelli et al. Transgenic mice expressing human transferrin as a model for meningococcal infection. Infect Immun 2007;75(12):5609-14.

Zollinger et al., Importance of complement source in bactericidal activity of human antibody and murine monoclonal antibody to meningococcal group B polysaccharide. Infect Immun 1983;40(1):257-64.

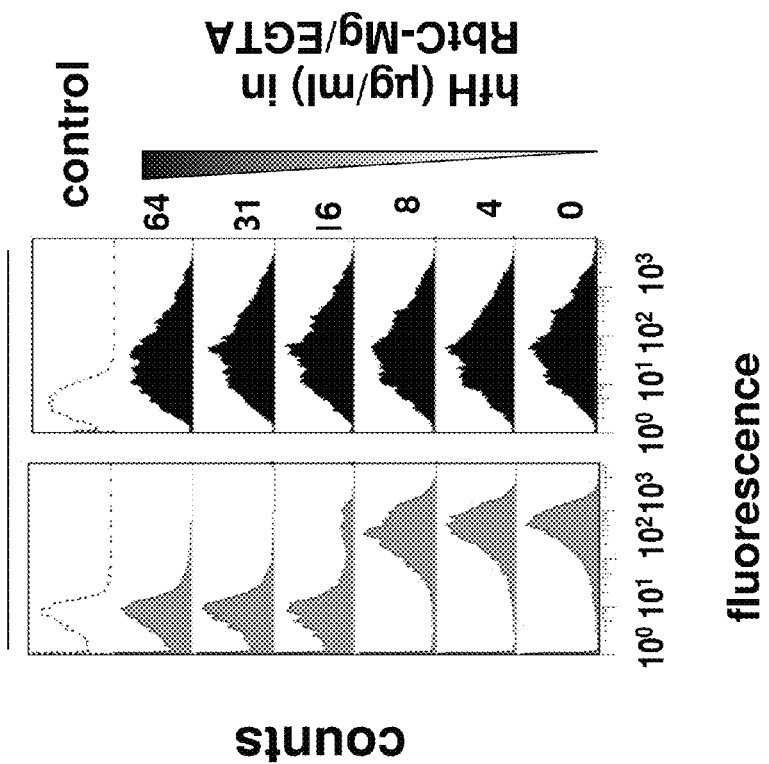
Figure 3 (con'd)
C

Figure 7 fH Short Consensus Repeat 6

| | | | | | | | | |
|---|---|---|---|---|---|---|---|---|
| (SEQ ID NO:1) | Human  | TLKPCDYPDI | KHGGLYHENM | RRPYFPVAVG | KYYSYYCDEH | FETPSGSYWD | HIHCTQDGWS |
| (SEQ ID NO:2) | Chimp  | ---------N- | ---------- | ---------- | ---------R | ---------- | Y--------- |
| (SEQ ID NO:3) | Rhesus | S--R------ | -----Y--S- | --------P- | --HF------ | -----A---- | Y--------- |
| (SEQ ID NO:4) | Rat    | ----EF--Q- | --N-----RR | -------PI- | --NE-----NG | ---L---L-- | YLR--EK--E |
| (SEQ ID NO:5) | Mouse  | -----EF-QF | -Y-R--Y-ES | L--N---SI- | -NK--K---NG | --SP---YS-- | YLR--AQGWE |

COMPLEMENT FACTOR H-BASED ASSAYS FOR SERUM BACTERICIDAL ACTIVITY AGAINST NEISSERIA MENINGITIDIS

CROSS-REFERENCE TO RELATED APPLICATION

This application claims the priority benefit of U.S. provisional Application Ser. No. 61/092,356, filed Aug. 27, 2008, which application is incorporated by reference in its entirety.

STATEMENT REGARDING FEDERALLY SPONSORED RESEARCH

This work was supported by National Institutes of Health grants RO1 AI46464 and RO1 AI054544 from the National Institute of Allergy and Infectious Diseases. The work at Children's Hospital Oakland Research Institute was performed in a facility funded by Research Facilities Improvement Program grant number CO6 RR-16226 from the National Center for Research Resources, NIH. The federal government has certain rights in this invention.

TECHNICAL FIELD

This invention relates to assays for bactericidal activity of antibodies against Neisseria meningitidis.

BACKGROUND

Neisseria meningitidis is a commensal organism that is found frequently in the throat of healthy adolescents (Maiden, M. C. et al. (2008) *J Infect Dis.*; Mueller, J. E. et al. (2007) *Emerg Infect Dis* 13:847-854; Trotter, C. L. et al. (2006) *Epidemiol Infect* 134:556-566; Bogaert, D. et al. (2005) *Clin Infect Dis* 40:899-902; Verdu, M. E. et al. (2001) *Epidemiol Infect* 127:245-259; Ala'Aldeen, D. A. et al. (2000) *J Clin Microbiol* 38:2311-2316). Rarely the organism invades the bloodstream and causes meningitis or rapidly fatal sepsis.

As far as is known, the organism is strictly a human pathogen. Reliable animal models of meningococcal disease have been difficult to develop (Lewis, T. et al. (1943) *J Clin Invest* 22:375-385; Ashton, F. E. et al. (1989) *Microb Pathog* 6:455-458; Zarantonelli, M. L. et al. (2007) *Infect Immun* 75:5609-5614). Many encapsulated strains of *N. meningitidis* that are highly pathogenic in humans are readily cleared from the bloodstream of commonly used experimental animals such as rabbits (Lewis, T. et al. (1943) *J Clin Invest* 22:375-385), mice (Zarantonelli, M. L. et al. (2007) *Infect Immun* 75:5609-5614; Oftung, F. et al. (1999) *FEMS Immunol Med Microbiol* 26:75-82; Holbein, B. E. et al. (1979) *Infect Immun* 24:545-551), or rats (variably, see, below). In addition, meningococcal strains have been reported to vary in their abilities to cause bacteremia in infant rats (see, e.g., Welsch, J. A. et al. (2004) *J Immunol* 172:5606-5615, Hou, V. C. et al. (2005) *J Infect Dis* 192:580-590; Toropainen, M. et al. (2005) *Vaccine* 23:4821-4833; Toropainen, M. et al. (2005) *Infect Immun* 73:4694-4703; Toropainen, M. et al. (2001) *Microb Pathog* 30:139-148; Toropainen, M. et al. (2006) *Infect Immun* 74:2803-2808).

*N. meningitidis* binds human complement factor H (fH) (Schneider, M. C., et al. (2006) *J Immunol* 176:7566-7575; Madico, G. et al. (2006) *J Immunol* 177:501-510), a molecule that down-regulates complement activation. Binding of human fH increases resistance of the organism to complement-mediated bacterial killing and may be an important mechanism that enables *N. meningitidis* to circumvent innate host defenses. With *N. gonorrhoeae*, binding of fH is restricted to human fH, which may in part explain species-specific restriction of natural gonococcal infection (Ngampasutadol, J. et al. (2008) *J Immunol* 180:3426-3435). The importance of serum fH on susceptibility of humans to meningococcal disease has been underscored by recent epidemiological observations that a single nucleotide polymorphism (C-496T) within a presumed NF-κB-responsive element in the promoter region of the cfH gene was associated with higher serum fH levels (C/C homozygous genotype) and an increased risk of acquiring meningococcal disease (Haralambous, E. et al. (2006) *Scand J Infect Dis* 38:764-771).

Considerable data indicate that serum complement-mediated bactericidal antibody confers protection against meningococcal disease (Goldschneider, I. et al. (1969) *J Exp Med* 129:1307-1326; I. et al. (1969) *J Exp Med* 129:1327-1348; Borrow, R. et al. (2005) *Vaccine* 23:2222-2227; Balmer, P. et al. (2004) *Expert Rev Vaccines* 3:77-87; Andrews, N et al. (2003) *Clin Diagn Lab Immunol* 10:780-786; Borrow, R. et al. (2001) *Infect Immun* 69:1568-1573). The minimum protective serum titer is estimated to be between 1:4 and 1:8 when measured with human complement. Assessment of bactericidal antibody titers has become a gold standard for assessing whether a human subject has mounted a protective immune response against *Neisseria*.

However, human complement is difficult to obtain (due in no small part to the fact that most human sera have naturally-acquired antibodies to *N. meningitidis*, which makes them unsuitable for serving as a source of human complement). Large numbers of healthy donors must be screened and their sera shown to lack antibody to provide suitable complement for use in the assays. Therefore, several standardized protocols for group A and C bactericidal assays use infant rabbit serum as a complement source instead of human serum (Maslanka, S. E. et al. (1997) *Clin Diagn Lab Immunol* 4:156-167; Jodar, L. et al. (2000) *Biologicals* 28:193-197). Assays using rabbit serum as a complement source have been widely used to infer vaccine effectiveness and as a basis of licensure of new meningococcal vaccines. Although rabbit complement was selected for these protocols because of greater ease of standardization, it has been known for many years that rabbit complement augments serum bactericidal titers as compared with titers measured with human complement (Zollinger, W. D. et al. (1983) *Infect Immun* 40:257-264; Santos, G. F. et al. (2001) *Clin Diagn Lab Immunol* 8:616-623). While serum bactericidal titers measured with rabbit complement have been correlated with the effectiveness of meningococcal vaccination introduced to large populations (Borrow, R. et al. (2005) *Vaccine* 23:2222-2227; Balmer, P. et al. (2004) *Expert Rev Vaccines* 3:77-87; N et al. (2003) *Clin Diagn Lab Immunol* 10:780-786), many of these sera would lack bactericidal activity if tested with human complement.

Thus, the correlations observed with rabbit complement may not accurately or totally reflect the actual mechanisms by which the vaccine-induced antibodies conferred protection. For example, the positive titers measured with rabbit complement could be a surrogate for alternative mechanisms of clearing *N. meningitidis* when human complement is present and antibody concentrations or quality are insufficient to elicit bactericidal activity but are sufficient to support opsonophagocytosis (Welsch, J. A. et al. (2007) *Clin Vaccine Immunol* 14:1596-1602; Plested, J. S. et al. (2008) *Clin Vaccine Immunol* 15:799-804).

SUMMARY

Assays for detection of bactericidal anti-Neisserial antibodies using a factor H polypeptide having a human amino acid sequence that mediates binding to Neisserial factor H binding protein (fHBp) are provided, as well as non-human animal models of Neisserial infection.

The present disclosure thus provides methods for detection of bactericidal anti-*Neisseria* antibodies in a sample, the method comprising combining in a reaction mixture a sample suspected of containing bactericidal anti-Neisserial antibodies, a fH polypeptide comprising an amino acid sequence of a human Short Consensus Repeat 6 (SCR 6), a source of non-human complement, and a *Neisseria* bacterium; and detecting the presence or absence of bactericidal anti-Neisserial antibodies in the sample by assessing viability of the *Neisseria* bacterium, wherein decreased viability of the *Neisseria* bacterium in the presence of the sample indicates the sample contains bactericidal anti-*Neisseria* antibodies. In related embodiments, the fH polypeptide is a human fH polypeptide. In other embodiments, the fH polypeptide is a chimeric fH polypeptide comprising an amino acid sequence of an fH polypeptide endogenous to the non-human animal modified to contain the amino acid sequence of the human SCR6. The non-human complement can be, for example, rabbit complement, rat complement or mouse complement. In further related embodiments, the *Neisseria* bacterium is *Neisseria meningitidis*, which can be of any capsular group, e.g., Group A, B, C, X, Y or W-135. In embodiments of interest, the sample is human serum.

The present disclosure also provides reaction mixtures comprising a sample suspected of containing bactericidal anti-Neisserial antibodies; an isolated factor H (fH) polypeptide comprising an amino acid sequence of a human Conserved Sequence Repeat 6 (SCR 6) (i.e., other than fH that may be present naturally in the sample to be tested), non-human complement, and a *Neisseria* bacterium. In related embodiments, the fH polypeptide is a human fH polypeptide. In other embodiments, the fH polypeptide is chimeric fH polypeptide comprising an amino acid sequence of a fH polypeptide endogenous to the non-human animal modified to contain the amino acid sequence of the human SCR6. The non-human complement can be, for example, rabbit complement, rat complement or mouse complement. In further related embodiments, the *Neisseria* bacterium is *Neisseria meningitidis*, which can be of any capsular group, e.g., Group A, B, C, X, Y or W-135. In embodiments of interest, the sample is human serum.

The present disclosure also provides kits comprising one or more vials containing an isolated factor H (fH) polypeptide comprising an amino acid sequence of a human Short Consensus Repeat 6 (SCR 6); and non-human complement. The kits can also include a culture of a *Neisseria* bacterium for use as a target in detection of bactericidal antibodies. In related embodiments, the fH polypeptide is a human fH polypeptide and/or can be a chimeric fH polypeptide comprising an amino acid sequence of a fH polypeptide endogenous to the non-human animal modified to contain the amino acid sequence of the human SCR6. The non-human complement of the kit can be, for example, rabbit complement, rat complement, or mouse complement.

The present disclosure also provides a non-human animal comprising a genomically integrated nucleic acid encoding a factor H (fH) polypeptide comprising an amino acid sequence of a human Short Consensus Repeat 6 (SCR 6), wherein the transgene is operably linked to a promoter to provide for expression of the nucleic acid in the non-human animal, wherein expression of the nucleic acid in the non-human animal provides for production of a fH polypeptide that binds a *Neisseria* bacterium. In related embodiments, the fH polypeptide is a human fH polypeptide and/or can be a chimeric fH polypeptide comprising an amino acid sequence of an fH polypeptide endogenous to the non-human animal modified to contain the amino acid sequence of the human SCR6. The non-human animal can be, for example, a rat or mouse. In some embodiments, the non-human animal is infected with a *Neisseria* bacterium, e.g., *Neisseria meningitidis*. Such non-human animal models can be used in methods of screening for a candidate agent having activity against *Neisseria*, wherein such method generally comprise administering a candidate agent to the non-human animal either prior to, during or after infection with a *Neisseria* bacterium, and detecting the presence or absence of production of bactericidal anti-Neisserial antibodies.

The present disclosure also provides a non-human animal model of Neisserial infection, comprising a non-human animal host comprising a factor H (fH) polypeptide comprising an amino acid sequence of a human Short Consensus Repeat 6 (SCR 6), wherein the fH polypeptide is present in the bloodstream of the non-human animal host; and a bacterial infection with a *Neisseria* bacterium, wherein the fH polypeptide is present in serum of the non-human animal. The fH polypeptide can be encoded by a nucleic acid integrated in the genome of the non-human animal (and thus is expressed into the bloodstream) and/or can be provided by administration to the bloodstream of the non-human animal host from an exogenous source. The fH polypeptide can be a human fH polypeptide or a chimeric fH polypeptide comprising an amino acid sequence of an fH polpeptide endogenous to the non-human animal modified to contain the amino acid sequence of the human SCR6. The non-human animal host can be, e.g., a rat or mouse. The *Neisseria* bacterium can be a *Neisseria meningitidis* strain of interest.

The present disclosure also provides methods of using non-human animal models of Neisserial infection described herein to screen for a candidate agent for promoting anti-*Neisseria* activity which comprise administering a candidate agent to the non-human animal infected with *Neisseria* and detecting the presence or absence of an effect of the candidate agent upon viability of *Neisseria* in the non-human animal.

Other aspects and embodiments will be readily apparent to the ordinarily skilled artisan upon reading the present disclosure.

BRIEF DESCRIPTION OF THE DRAWINGS

FIG. 7 illustrates the amino acid sequence of the short consensus repeat 6 (SCR6) of fH of human, chimp, rhesus macaque, rat, and mouse. Residues indicated by dashes are identical to the corresponding residue in the human fH amino acid sequence.

FIG. 8 shows Western blots for expression of human fH in Wistar rat pups (F0 generation). The blots were probed with anti-human fH antibody and human serum was loaded as a positive control.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent such publications may set out definitions of a term that conflicts with the explicit or implicit definition of the present disclosure, the definition of the present disclosure controls.

It must be noted that as used herein and in the appended claims, the singular forms "a", "an", and "the" include plural referents unless the context clearly dictates otherwise. Thus, for example, reference to "a polypeptide" includes a plurality of such polypeptides and reference to "the bacterium" includes reference to one or more bacteria, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

Assays for detection of bactericidal anti-Neisserial antibodies using a factor H polypeptide having a human amino acid sequence that mediates binding to Neisserial factor H binding protein (fhBp) are provided, as well as non-human animal models of Neisserial infection.

DEFINITIONS

"Complement" refers to a collection of serum proteins that provide for a functional complement cascade, which is the biochemical cascade that promotes bacterial death. As such, "complement" as used herein refers to a collection of serum proteins that can mediate a functional complement cascade associated with the classical pathway, the alternative pathway, or both, and may further include serum proteins that can mediate the mannose-binding lectin pathway.

"Non-human complement" refers to complement from a source other than human, usually a mammalian source and includes, but is not necessarily limited to, rodent complement (e.g., rat complement, mouse complement, rabbit complement), and non-human primate complement (e.g., chimpanzee complement, monkey complement), and the like.

Figure 1:
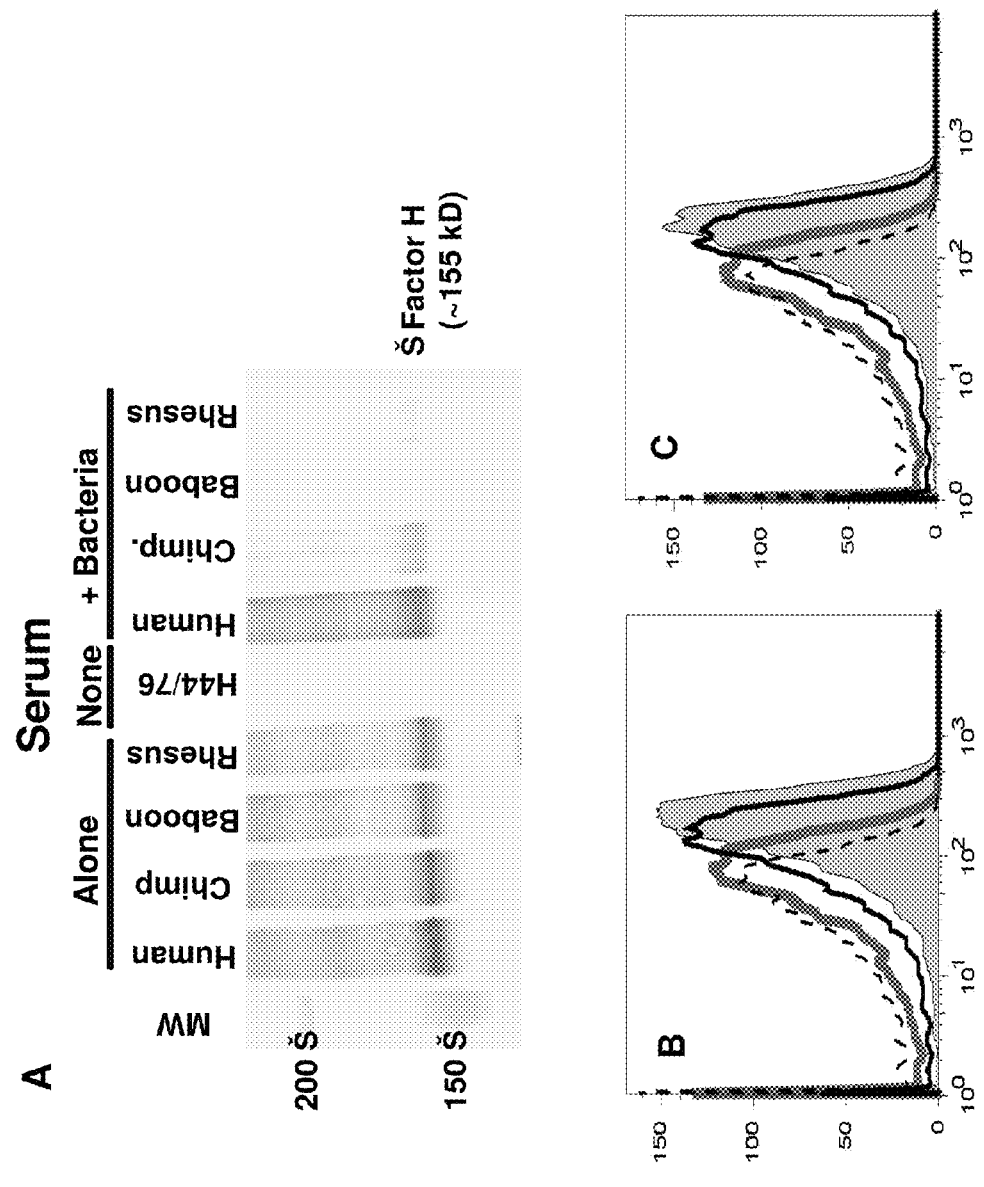
FIG. 1, Panels A-C depict the species specificity of fH binding to *N. meningitidis*. (Panel A) Binding of primate fH to *N. meningitidis* strain H44/76 as measured by Western blot. The ability of anti-human fH antibody to recognize fH from chimpanzee, baboon and rhesus macaque serum is shown in the lanes marked 'serum alone', which contains heat-inactivated serum from each of the primates at a 1:100 dilution. The lanes marked 'serum+bacteria' contain H44/76 that was incubated with the respective primate sera and the lane with 'H44/76 and no serum ('none') contains bacteria alone. (Panel B) and (Panel C) Effect of addition of rat (Panel B) or rabbit (Panel C) serum on binding of biotinylated human fH to *N. meningitidis* bacterial cells as measured by flow cytometry. Dashed line, bacterial cells in the absence of added biotinylated human fH. Solid black line, binding of biotinylated human fH in absence of added sera. Solid gray line, binding of biotinylated human fH in presence of 40 percent heat-inactivated human serum. Filled light gray area, binding of biotinylated human fH in the presence of 40 percent heat-inactivated rat or rabbit serum. Similar inhibition of binding of biotinylated human fH in the presence human serum but not by rat and rabbit sera was observed in three independent experiments.

"Bactericidal antibody" as used herein refers to an antibody that facilitates complement-mediated killing of a bacterium.

"Factor H Binding Protein" (fHBP), which is also known in the literature as GNA1870, GNA 1870, ORF2086, LP2086 (lipoprotein 2086), and "741" refers to a polypeptide of *Neisseria*, e.g., *Neisseria meningitidis*, presented on the surface of the bacterium. *N. meningitidis* strains have been sub-divided into three fHBP variant groups (referred to as variant 1 (v.1), variant 2 (v.2), and variant 3 (v.3) in some reports (Masignani et al. 2003, supra) and Family A and B in other reports (see, e.g., Fletcher et al. 2004 Infect Immun 2088-2100)) based on amino acid sequence variability and immunologic cross-reactivity (Masignani et al. J Exp Med 2003; 197:789-99). For clarity, the present disclosure uses the v.1, v.2 and v.3 terminology. Because the length of variant 2 (v.2) fHBP protein (from strain 8047) and variant 3 (v.3) fHBP (from strain M1239) differ by −1 and +7 amino acid residues, respectively, from that of MC58, the numbering used to refer to residues for v.2 and v.3 fHBP proteins differs from numbering based on the actual amino acid sequences of these proteins.

"Isolated" refers to a compound of interest (e.g., fH polypeptide) that, if naturally occurring, is in an environment different from that in which it may naturally occur. "Isolated" is meant to include compounds that are within samples that are substantially enriched for the compound of interest and/or in which the compound of interest is partially or substantially purified. Where the compound is not naturally occurring, "isolated" indicates the compound has been separated from an environment in which it was made by either synthetic or recombinant means.

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, chimeric polypeptide, and the like).

"Substantially pure" indicates that an entity (e.g., polypeptide) makes up greater than about 50% of the total content of the composition (e.g., total protein of the composition) and typically, greater than about 60% of the total protein content. More typically, "substantially pure" refers to compositions in which at least 75%, at least 75%, at least 85%, at least 90% or more of the total composition is the entity of interest (e.g., of the total protein). Preferably, the protein will make up greater than about 90%, and more preferably, greater than about 95% of the total protein in the composition.

The term "heterologous" refers to two components that are defined by structures derived from different sources. For example, where "heterologous" is used in the context of a chimeric polypeptide, the chimeric polypeptide includes operably linked amino acid sequences that can be derived from different polypeptides (e.g., a first component from a fH polypeptide of a first origin (e.g., human) and a second component from a fH polypeptide of a second origin (e.g., rabbit)). Similarly, "heterologous" in the context of a polynucleotide encoding a chimeric polypeptide includes operably linked nucleic acid sequence that can be derived from different genes. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding a fH polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present.

"Heterologous" as used herein in the context of a chimeric fH polypeptide indicates that the chimeric fH polypeptide contains operably linked and contiguous amino acid sequences of structural elements of at least two different fH polypeptides of different origins. For example, a "heterologous fH polypeptide" includes those having rabbit fH polypeptide amino acid sequences flanking a CSR6 domain having a sequence of a human CSR6.

"Derived from" in the context of an amino acid sequence or polynucleotide sequence (e.g., an amino acid sequence "derived from" a human fH polypeptide) is meant to indicate that the polypeptide or nucleic acid has a sequence that is based on that of a reference polypeptide or nucleic acid (e.g., a naturally occurring human fH polypeptide or encoding nucleic acid), and is not meant to be limiting as to the source or method in which the protein or nucleic acid is made. "Derived from" in the context of bacterial strains is meant to indicate that a strain was obtained through passage in vivo, or in in vitro culture, of a parental strain and/or is a recombinant cell obtained by modification of a parental strain.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans. (Goldschneider et al., 1969, J. Exp. Med. 129:1307; Borrow et al. 2001 Infect Immun. 69:1568).

The term "transgene" is used herein to describe genetic material which has been or is about to be artificially inserted into the genome of a non-human animal, and particularly into a cell of a living non-human mammal (e.g., rodent, e.g., rat, mouse).

The term "transgenic animal" means a non-human animal having a transgenic element integrated in the genome of one or more cells of the animal. "Transgenic animals" as used herein thus encompasses animals having all or nearly all cells containing a genetic modification (e.g., fully transgenic animals, particularly transgenic animals having a heritable transgene) as well as chimeric, transgenic animals, in which a subset of cells of the animal are modified to contain the genomically integrated transgene.

A "knock-out" of a target gene means an alteration in the sequence of the gene that results in a decrease of function of the target gene. "Knock-outs" of particular interest are those in which target gene expression is undetectable or insignificant. For example, a knock-out of a receptor gene means that function of the receptor has been substantially decreased so that receptor activity in binding its normal ligand is not detectable or at insignificant levels. Decrease in function can be due to decreased production of a full-length gene product as a result of the genetic alteration, or production of an altered gene product that is deficient in function relative to the native gene product. "Knock-out" transgenics of the invention can be transgenic animals having a heterozygous or homozygous knock-out of the target gene. "Knock-outs" also include conditional knock-outs, where alteration of the target gene can occur upon, for example, exposure of the animal to a substance that promotes target gene alteration.

A "knock-in" of a gene means the addition of a nucleic acid encoding a gene product of interest to the genome, which may be accompanied by a knock-out of a corresponding endogenous gene. Such "knocked-in" genes can be recombined into the genome so that it is regulated in a manner comparable to that of the endogenous gene. The transgene can be a modified version of the endogenous gene (e.g., as in a chimeric fH polypeptide). "Knock-in" transgenics can be heterozygous or homozygous for the genetic alteration. "Knock-ins" also encompass conditional knock-ins.

Overview

The present disclosure provides methods and compositions that exploit the observation that human factor H (fH) can mediate resistance of *N. meningitidis* to complement-mediated killing by non-human complement (e.g., rabbit complement, rat complement). This observation can be applied to provide assays that can assess complement-mediated killing by anti-*N. meningitidis* antibodies using human fH and a source of non-human complement so as to decrease the incidence and/or degree of false positive results (i.e., a result in which the assay indicates the sample contains, or contains a higher level of, bactericidal anti-*N. meningitidis* antibodies than it actually does). Addition of human fH to such assays more accurately mimics the in vivo situation in humans in that fH binds *N. meningitidis* and inhibits complement-mediated killing of the bacteria, thereby potentially frustrating the bactericidal activity of anti-*N. meningitidis* antibodies that may be present in human serum. The assays of the present disclosure provide the additional advantage that such assays are conducted using non-human complement (e.g., rat or rabbit complement), thereby avoiding the need to use human complement. Sources of human complement are expensive, due at least in part to the fact that such assays require that the human complement not contain anti-*N. meningitidis* antibodies, which could potentially increase the incidence of false positive results. Thus, the finding that isolated human fH can work in concert with non-human complement factors is exploited to provide an assay that is a more relevant reflection of human immunity and less expensive than convention assays using non-human complement.

The present disclosure also leverages the finding that human fH can function in the presence of non-human complement to provide a non-human animal model of *N. meningitidis* infection. Because non-human fH does not bind *N. meningitidis*, non-human fH does not provide resistance to complement-mediated killing, and infections of non-human animals with *N. meningitidis* are cleared thereby frustrating attempts to provide a non-human animal model of infection. The non-human animal models of the present invention provide for non-human animals having a *N. meningitidis*-binding fH. The "*N. meningitidis*-binding fH" refers to a fH which contains an amino acid sequence of human fH that mediates binding to *N. meningitidis*, i.e., the amino acid sequence of a human Short Consensus Repeat 6 (SCR 6), which is described in more detail below. Thus, the *N. meningitidis*-binding fH may be a human fH, which can be provided by administration of human fH (e.g, parenteral administration, e.g., intravenous, intraperitoneal, subcutaneous) either prior to, with, or after administration of a *Neisseria* (e.g, *Neisseria meningitidis*) bacterial inoculum in, for example, an in vivo mouse or infant rat model of passive protection (e.g., using a parenteral (e.g., intravenous, intraperitoneal or intranasal challenge), by expression from a human fH-encoding transgene present in the non-human animal, by "humanization" of the SCR 6 amino acid sequence of a fH-encoding gene of the non-human animal, and/or by expression of such a "humanized" fH from a transgene present in the non-human animal.

Exemplary embodiments are described in more detail below.

Factor H (fHbp) Polypeptide

"Factor H polypeptide", "factor H", "complement factor H", "factor H protein", "fH", "fH protein", and fH polypeptide" are used interchangeably herein to refer to a polypeptide that modulates a complement pathway and, when it contains a short consensus repeat domain 6 (SCR6) of a human fH polypeptide, is bound by *Neisseria*, e.g., through the Neisserial protein factor H binding protein (fHbp). In humans, factor H is a member of the Regulator of Complement Activation (RCA) gene cluster and encodes a protein with twenty short consensus repeat (SCR) domains. In vivo, fH is secreted into the bloodstream and has a role in the regulation of complement activation, and plays a particular role in clearance of bacterial infections.

"A factor H (fH) polypeptide comprising an amino acid sequence of a human Short Consensus Repeat 6 (SCR6)" refers to a polypeptide comprising an amino acid sequence of an fH polypeptide which contains or is modified to contain a short consensus repeat domain 6 (SCR6) having an amino acid sequence of a human SCR6 of human fH polypeptide. Thus "A fH polypeptide comprising an amino acid sequence of a human SCR6" includes fully human fH polypeptide and fragments thereof, as well as chimeric polypeptides comprising a human SCR6 amino acid sequence operably linked to non-human fH amino acid sequences, with the proviso that the polypeptides has activity in binding factor H binding protein (fHbp) of *Neisseria* (e.g., *Neisseria meningitidis*).

The term "short consensus repeat domain 6", also referred to interchangeably herein as "short consensus repeat 6" and "SCR6" refers to a polypeptide domain of factor H that, in human factor H, confers binding of factor H to fHbp of *Neisseria*. "Human SCR6" refers to a polypeptide (as well as nucleic acid encoding such a polypeptide, as will be evident from context of use) having an amino acid sequence of SEQ ID NO:1. The amino acid sequences of SCR6 of chimp (SEQ ID NO:2), rhesus macaque monkey (SEQ ID NO:3), rat (SEQ ID NO:4), and mouse (SEQ ID NO:5) are depicted in FIG. 7.

fH polypeptides suitable for use in the methods described herein can be obtained from any suitable source. For example, where the fH polypeptide is a human fH polypeptide, the human fH polypeptide can be obtained by isolation from a source that naturally produces the polypeptide or is genetically modified to produce the polypeptide (e.g., a recombinant source).

Nucleic acid encoding fH polypeptides of a variety of mammalian sources are known, as are the nucleic acid sequences and amino acid sequence of the encoded fH polypeptide. Human fH polypeptides and their encoding nucleic acids are described at, for example, GenBank Accession No. NM_000186, with alternatively spliced polypeptide variants described at Genbank Accession No. NM_001014975. Other exemplary mammalian fH polypeptides (nucleic acid and polypeptide sequences) are known in the art and include, but are not limited to, mouse (Genbank Acc. No. NM_009888), rat, primate (e.g., chimpanzee, monkey (e.g., rhesus macaque)), and sheep (GenBank Acc. No. EU888587).

Chimeric fH polypeptides containing a human CSR6 amino acid sequence can be engineered by any suitable methods available and known in the art. For example, the coding sequence of nucleic acid encoding a mammalian, non-human fH polypeptide can be replaced with a nucleic acid fragment encoding a human SCR6 using recombinant methods that are well known in the art. Alternatively or in addition such chimeric fH polypeptides can be produced through site-directed mutagenesis to modify the coding sequence so as to encode amino acid residues of the human SCR6. Other techniques available include nucleic acid amplification of an fH-encoding DNA, and cloning of amplified sequence or digested fragment into a vector containing a promoter and a polyA tail to create a fH-encoding construct. fH polypeptides, including chimeric fH polypeptides, can be produced by sytheic techniques where applicable.

Nucleic acid constructs can be expressed as proteins either in vitro or in vivo using standard protein expression methods well known in the art to generate the chimeric polypeptide comprising human SCR6. Such engineered nucleic acid constructs may also be introduced into the genomes of non-human animals for expression as a transgenic gene product.

Production methods of fH polypeptides can involve any suitable construct and any suitable host cell, which can be a prokaryotic or eukaryotic cell, usually a mammalian, bacterial or yeast host cell. Methods for introduction of genetic material into host cells include, for example, transformation, electroporation, conjugation, calcium phosphate methods and the like. The method for transfer can be selected so as to provide for stable expression of the introduced fH polypeptide-encoding nucleic acid. Such nucleic acid can be provided as an inheritable episomal element (e.g., plasmid) or can be genomically integrated.

Suitable vectors for transferring nucleic acids of interest can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

In one embodiment, the vector is an expression vector based on episomal plasmids containing selectable drug resistance markers and elements that provide for autonomous replication in different host cells (e.g., in both *E. coli* and *N. meningitidis*). One example of such a "shuttle vector" is the plasmid pFP10 (Pagotto et al. Gene 2000 244:13-19).

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a chimeric fHBP, may provide for propagating the subject nucleic acids, or both.

Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgt10, λgt11, λgt18-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

For expression of an fH polypeptide of interest, an expression cassette may be employed. Thus, the present disclosure provides a recombinant expression vector comprising a subject nucleic acid. The expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to a naturally-occurring fH polypeptide, or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a procaryotic host for cloning and amplification. In addition the expression construct may contain a selectable marker gene to allow the selection of transformed host cells. Selection genes are well known in the art and will vary with the host cell used.

It should be noted that recombinant fH polypeptides may comprise additional elements, such as a detectable label, e.g., a radioactive label, a fluorescent label, a biotin label, an immunologically detectable label (e.g., an HA tag, a poly-Histidine tag) and the like. Such additional elements can be provided to facilitate isolation (e.g., biotin tag, immunologically detectable tag) through various methods (e.g., affinity capture, etc.).

Isolation and purification of a polypeptide to interest can be accomplished according to methods known in the art. For example, fH polypeptide can be isolated from a lysate of cells genetically modified to express the fH polypeptide by immunoaffinity purification, which generally involves contacting the sample with an anti-fH polypeptide antibody, washing to remove non-specifically bound material, and eluting specifically bound fH polypeptide. Isolated fH polypeptide can be further purified by dialysis and other methods normally employed in protein purification methods. Purified fH polypeptide can be provided such that the polypeptide is present in a composition that is substantially free of other expressed polypeptides, e.g., less than 90%, usually less than 60% and more usually less than 50% of the composition is made up of other expressed polypeptides.

Assays for Detection of Bactericidal Anti-*N. meningitidis* Antibodies

As noted above, the present disclosure provides methods and compositions for the detection of bactericidal anti-*Neisseria* antibodies in a sample. Assays are provided that assess complement-mediated killing by anti-*N. meningitidis* antibodies using isolated factor H polypeptide comprising an amino acid sequence of human Short Consensus Repeat 6 (SCR6) and non-human complement. Such assays can provide for decreased incidence and/or degree of false positive results (i.e., a result in which the assay indicates the sample contains, or contains a higher level of, bactericidal anti-*N. meningitidis* antibodies than the sample actually does). Addition of isolated factor H polypeptide comprising human SCR6 to such assays more accurately mimics the in vivo situation in humans than traditional assays because the SCR6 domain of human fH binds *N. meningitidis* and inhibits complement-mediated killing of the bacteria, thereby potentially frustrating the bactericidal activity of anti-*N. meningitidis* antibodies that may be present in human serum. The assays of the present disclosure provide the additional advantage that such assays are conducted using non-human complement (e.g., rat or rabbit complement), thereby avoiding the need to use human complement. Thus, the finding that human fH can work in concert with non-human complement factors is exploited to provide an assay that is more accurate and less expensive than conventional assays using human complement.

The method generally involves combining, in a reaction mixture, a sample suspected of containing bactericidal anti-Neisserial antibodies, an isolated factor H polypeptide comprising an amino acid sequence of human Short Consensus Repeat 6 (SCR 6), non-human complement, and *Neisseria* bacterium, and assessing the viability of the *Neisseria* bacterium, wherein decreased viability of the *Neisseria* bacterium in the presence of the sample indicates the sample contains bactericidal anti-*Neisseria* antibodies.

Human fH or an isolated factor H polypeptide comprising an amino acid sequence of human Short Consensus Repeat 6 (SCR 6) is also useful in assaying opsonophagocytic activity of anti-Neisserial antibodies using non-human complement. Opsonophagocytic assay generally involves combining, in a reaction mixture, a sample suspected of containing opsonophagocytic anti-Neisserial antibodies, peripheral blood mononuclear leukocytes or a monocytic cell line grown in tissue culture as the phagocytic effector cells, an isolated factor H polypeptide comprising an amino acid sequence of human Short Consensus Repeat 6 (SCR 6), non-immune non-human complement, and *Neisseria* bacterium, and assessing the viability of the *Neisseria* bacterium, wherein decreased viability of the *Neisseria* bacterium in the presence of the sample indicates the sample contains opsonophagocytic anti-*Neisseria* antibodies. The test sample (i.e., the sample being assayed for presence of opsonophagocytic anti-Neisserial antibodies) is heat inactivated to remove any internal complement activity. Assays for measuring activity of opsonophagocytic activity and their use in assessing anti-Neisserial antibodies are described in Plested J. S. and Granoff D. M., Clin Vaccine Immunol 2008, 15(5): 799-804 and Granoff D M, Vaccine, 2009 (Relative importance of complement-mediated bactericidal and opsonic activity for protection against meningococcal disease. Doi: 10.1016/j.vaccine.2009.04.066).

Samples

Any sample suspected of containing bactericidal anti-Neisserial antibodies may be assayed, for example a biological sample, e.g., obtained from a subject (e.g., blood or blood fraction (e.g., serum), mucosal secretion, tissue, and the like), from cell culture (e.g., from supernatant of a antibody-secreting cell (e.g., hybridoma)). The serum sample may be diluted in a buffer, e.g. Dulbecco's buffer, and may be tested as serial dilutions to facilitate assessment of antibody titer. Typically, where the sample may contain complement (e.g., as in a serum sample), the sample is treated to inactivate endogenous complement, e.g., by heating (e.g., at 56° C. for about 30 minutes). Samples can be fresh or frozen prior to use. Where samples are assessed to determine effectiveness of a vaccine to elicit bactericidal anti-Neisserial antibodies, the samples can be obtained prior to and after immunization of a subject.

Non-Human Complement

Non-human complement for use in the assay can be from any suitable source, usually a mammalian source. Exemplary sources of complement include lagomorphs (e.g., rabbits), rodents (rats, mice, guinea pigs, hamsters, and the like), ungulates (e.g., cattle, sheep, goats, pigs), and non-human primates (monkeys, apes, chimpanzees), and may be infant animals (e.g., infant rabbits, infant rats, etc.). Non-human complement is commercially available or can be readily obtained from serum according to methods known in the art. In general the non-human complement contains or is treated so that it contains no detectable bactericidal activity. This can be accomplished by, for example, by using sera from young animals, or by treating the non-human sera from older animals to deplete antibodies prior to use in the assay (e.g., using an anti-IgG affinity column). The amount of non-human complement in the assay can be varied among samples as a control, or can be provided in the approximately same amount in each sample tested (e.g., as a standard). For example, the reaction mixture can contain about 10% to 25% (vol/vol) of non-human complement in serum.

The non-human complement can be added to reaction mixtures in different amounts to provide for reaction samples having different, known amounts of non-human complement. Such samples can be assayed in parallel to facilitate detection of bactericidal antibody titers.

*Neisseria* Bacteria

Any suitable *Neisseria*, particularly a *Neisseria* bacteria expressing a surface fHbp, can be used as the target bacterium for detection of bactericidal antibodies in the assays described herein. Such *Neisseria* bacteria include *Neisseria meningitidis* and *N. gonorrhea*. The target bacterium can be selected in accordance with the specifically of the bactericidal antibodies to be assayed. For example, where the assay is to provide for detection of bactericidal anti-*Neisseria meningitidis* antibodies, the target bacterium can be any suitable *Neisseria meningitidis*, e.g., Group A, B, C, X, Y, or W-135, or *Neisseria meningitidis* of any other capsular group of interest, a *Neisseria meningitidis* strain expressing a particular antigen of interest (e.g., v.1, v.2, or v.3 fHbp, including fHbp subvariants; PorA type, and the like). The assay can be used in connection with *Neisseria* genetically modified to express an antigen of interest. For example, the target bacterium can be selected to facilitate analysis of production of bactericidal anti-Neisserial antibodies following immunization with a vaccine.

Prior to use in the assay, the target bacteria may be cultured by methods known in the art, for example, in broth (e.g., Mueller-Hinton broth) or on an agar plate (e.g., chocolate agar plates). If cultured on an agar plate, the bacteria is removed from the agar plate and resuspended. If cultured in liquid broth, the bacteria can be centrifuged and resuspended. In general, the bacteria are provided to a desired cell number, and can be provided in samples of differing cell numbers as a control. For example, bacteria can be resuspended at a cell density of about $10^5$ to $10^8$ colony forming units (CFU)/ml, usually about $5 \times 10^7$ CFU/ml. The resuspension solution can be selected so as to be compatible for use with the detection assay, e.g., a buffer, typically HBSS (Hanks Basic Salt Solution) or phosphate buffered saline (PBS) supplemented with $MgCl_2$ and $CaCl_2$.

Prior to use in the assay, the bacteria may be washed one or more times to remove components of culture broth. For example, the bacteria may be washed in buffer (e.g., containing bovine serum albumin) and/or in heat-inactivated serum (e.g., depleted for IgG, e.g., so as to contain no detectable IgG). Washing generally involves resuspending the bacteria in a solution, pelleting the bacterial cells by centrifugation, and resuspending the bacteria, e.g., in reaction mixture buffer for use in the assay.

fH Polypeptide

Any suitable fH polypeptide having an amino acid sequence of a human SCR6 as described herein is used in the assays. Of particular interest is used of a fully human fH polypeptide of a fragment thereof that retains activity in binding to fHbp and in modulating the complement cascade. The crystal structure of several domains of factor H, including SCR6, has been solved and can provide guidance for production of fragments of interest. fH polypeptide can be added to the reaction mixture in any suitable amount, e.g., from about 5 to 6 µg/ml, 10 µg/ml, 12 µg/ml, 20 µg/ml, 25 µg/ml, 50 µg/ml or more. The amount used can vary depending on whether the reaction mixture contains a calcium chelator (e.g., to examine the alternative pathway separate from the classical pathway of complement activity).

Reaction Mixtures

Reaction mixtures of the assays are prepared by combining, in any suitable order, assay reagents (which comprise an isolated factor H (fH) polypeptide comprising an amino acid sequence of human SCR6 and non-human complement), a *Neisseria* bacterium and a test sample. The reaction mixture can be produced by combining these components in any suitable vessel, such as a test tube, the well of a plate, or a capillary tube. In general, the reaction mixture is suspended in buffer, particularly a physiologically compatible buffer, e.g., PBS or other suitable buffer exemplified herein. Reaction volumes of the reaction mixture can vary, and are usually on the order of microliters to milliliters (e.g. 100 µl, 500 µl, 1 ml, and the like) The sample can be provided in different dilutions in the reaction mixture, e.g., 1:2, 1:4, 1:6, 1:8, 1:10, 1:12, 1:14, 1:16, 1:18, 1:20, 1:22, 1:24, or greater and the like with dilutions of 1:4 and greater being of interest.

The reaction mixture is incubated under conditions suitable for complement-mediated bactericidal antibody activity. For example, the reaction mixture can be incubated for a time sufficient to allow for complement-mediated bactericidal antibody activity (e.g., from about 15 min to 90 min, about 30 min to 90 min, and the like) and at a suitable temperature (e.g., ambient temperature or physiologically relevant temperature (e.g., about 37° C.)). In addition to test samples, control samples can be provided. Such control samples can include negative control samples (e.g., samples that parallel the conditions of test samples, but to which no biological sample is added, no fH is added, no non-human complement is added, or to which an antibody having no detectable bactericidal activity is added) and/or positive controls (e.g., samples that parallel the conditions of test samples, but to which an antibody having known bactericidal activity for the target bacterium is added).

Detection

Following incubation with test sample, the presence or absence of bactericidal anti-Neisserial antibodies is detected by assessing the viability of *Neisseria* in the reaction mixtures. This can be accomplished by, for example, plating the reaction mixture on a suitable medium (e.g., agar plates) and assessing colony forming units, culturing the reaction mixture in broth and assessing bacterial growth by cell density (e.g., by spectrophotometic absorption), FACS (see, e.g., Mountzouros et al. "Detection of Complement Mediated Antibody-Dependent Bactericidal Activity in a Fluorescence-Based Serum Bactericidal Assay for Group B *Neisseria meningitidis*" (2000) J. Clin. Microbiol. 38:2878-2884), and the like. The bactericidal titer is defined as the serum dilution at which a decrease in viable *Neisseria* is observed (e.g., a decrease in CFU per milliliter), typically a dilution resulting in a 50% or 90% decrease in viability (e.g., a 50% decrease in CFU per milliliter) as compared to a control at time zero (or after 60 min or whatever incubation in negative control sera). Results can also be described as 50% survival compared to survival at time zero.

One ordinarily skilled in the art will appreciate the need for control reaction mixtures to be performed in parallel with the experimental reaction mixture. For example, samples containing known titers (ranging from low to high) of bactericidal antibodies can be assayed as positive controls. In addition, a reaction mixture to which no sample has been added should be performed, as well as a reaction mixture to which no non-human complement has been added. A reaction mixture containing non-human fH polypeptide instead of a factor H (fH) polypeptide comprising an amino acid sequence of human SCR6 may also be performed in parallel, to confirm that the factor H (fH) polypeptide comprising an amino acid sequence of human SCR6 is attenuating complement-mediated toxicity against *Neisseria*.

Kits

The present disclosure also provides kits for use in the assays described herein. Such kits can include, for example, an fH polypeptide having an amino acid sequence of a human CSR6 (e.g, a human fH polypeptide), non-human complement, and, optionally, a target *Neisseria* bacterium. The reagents can be provided in separate vials or at least the fH polypeptide and non-human complement can be provided in a single vial. The kit can optionally include reagents for use in control assays as described above.

In addition to above-mentioned components, the kit can further include instructions for using the components of the kit to practice the assays described herein. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. The instructions can be provided on an electronic storage data file present on a suitable computer readable storage medium, e.g. CD-ROM, diskette, etc. In some embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control reagent mixtures, e.g., an antibody having a known complement-mediated bactericidal activity for a *Neisseria* bacterium (either positive for bactericidal activity or having no detectable bactericidal activity), and the like.

Non-Human Animal Models

As noted above, the present disclosure also leverages the finding that human fH can function in the presence of non-human complement to provide a non-human animal model of *N. meningitidis* infection. Because non-human fH does not detectably or significantly bind *N. meningitidis*, non-human fH does not provide resistance to complement-mediated killing, and infections of non-human animals with *N. meningitidis* are cleared thereby frustrating attempts to provide a non-human animal model of infection.

The non-human animal models of the present disclosure provide for non-human animals having an *N. meningitidis*-binding fH. The "*N. meningitidis*-binding fH" refers to a fH which contains an amino acid sequence of human fH that mediates binding to *N. meningitidis*, i.e., the amino acid sequence of a human Short Consensus Repeat domain 6 (SCR6), which is described in more detail below. Thus, the *N. meningitidis*-binding fH may be a human fH, which can be provided by administration of fH (e.g, intravenous administration), expression from a human fH-encoding nucleic acid sequence present in the non-human animal, or by expression of a non-human fH-encoding nucleic acid that has been "humanized" to comprise sequence encoding the human SCR6 domain instead of or in addition to the endogenous SCR6 domain. Human fH-encoding nucleic acid, as well as chimeric fH polypeptide-encoding nucleic acids, for expression in a non-human animal can be obtained using any suitable techniques as discussed above.

Transgenic Animals

Methods for production of transgenic animals modified to express an fH polypeptide are well known in the art. Exemplary methods include those described in Transgenic Animal Generation and Use L. M. Houdebine, Harwood Academic Press, 1997; Transgenesis Techniques: Principles and Protocols D. Murphy and D. A. Carter, ed. (June 1993) Humana Press; Transgenic Animal Technology: A Laboratory Handbook C. A. Pinkert, ed. (January 1994) Academic Press; Transgenic Animals F. Grosveld and G Kollias, eds. (July 1992) Academic Press; and Embryonal Stem Cells: Introducing Planned Changes into the Animal Germline M. L. Hooper (January 1993) Gordon & Breach Science Pub; U.S. Pat. No. 6,344,596; U.S. Pat. No. 6,271,436; U.S. Pat. No. 6,218,596; and U.S. Pat. No. 6,204,431; Maga and Murray (1995) Bio/Technol. 13:1452-1457; Ebert et al. (1991) Bio/Technol. 9:835-838; Velander et al. (1992) Proc. Natl. Acad. Sci. USA 89:12003-12007; Wright et al. (1991) Bio/Technol. 9:830-834.

Transgenic animals also can be generated using methods of nuclear transfer or cloning using embryonic or adult cell lines as described for example in Campbell et al. (1996) Nature 380: 64-66; and Wilmut et al. (1997) Nature 385: 810-813. Cytoplasmic injection of DNA can be used, as described in U.S. Pat. No. 5,523,222. Subject transgenic animals can be obtained by introducing a construct comprising stearoyl CoA desaturase-encoding sequences.

Transgenic animals also include somatic transgenic animals, e.g., transgenic animals that include a transgene in somatic cells (and not in germ line cells). For example, the mammary gland cells of an animal are transformed with a stearoyl CoA desaturase transgene, and the transgene is expressed in mammary cells of the animal. Methods of somatic cell transformation are described in the art. See, e.g., Furth et al. (1995) Mol. Biotechnol. 4:121-127.

Any non-human animal having a genome susceptible to modification can be genetically modified using the methods and systems of the invention to produce a transgenic animal. The non-human animal can be a vertebrate or an invertebrate, and may be mammalian or non-mammalian (e.g., avian species (e.g., chickens). Exemplary non-human mammalian subjects include, but are not necessarily limited to, non-human primates (monkeys, apes, chimpanzees), rodents (rats, mice, guinea pigs, hamsters, and the like), lagomorphs (e.g., rabbits), and ungulates (e.g., cattle, sheep, goats, pigs). The term "ungulate" is used to mean any species or subspecies of porcine (pig), bovine (cattle), ovine (sheep) and caprine (goats).

Engineering of a non-human fH-encoding nucleic acid sequence that has been "humanized" to comprise sequence encoding the human SCR6 domain for expression in a non-human animal can be performed using cloning methods that are well known in the art. For example, to engineer a mouse fH-encoding nucleic acid sequence such that it comprises sequence encoding the human SCR6 domain instead of the mouse SCR6, the nucleic acid sequence encoding mouse SCR6 polypeptide can be removed from the mouse fH CDS (annotated in Genbank Acc. No. NM_009888) using restriction digestion enzymes, and replaced with the nucleic acid sequence encoding human SCR6 polypeptide using ligation enzymes.

A nucleic acid sequence that has been engineered for expression in a non-human animal can be provided with an operably linked sequence to regulate its expression, e.g. a promoter sequence. The nucleic acid sequences of the embodiments described herein can be engineered to contain any of a variety of promoters known in the art to regulate the expression of the nucleic acid sequences. For example, the nucleic acid sequences can be engineered such that nucleic acid expression is regulated by the fH promoter, or by a tissue- or cell-specific promoter, or by a promoter that is regulated by a signaling pathway, e.g. activation of the estrogen receptor, or a drug, e.g. tetracycline.

The human-fH-encoding nucleic acid sequence or the chimeric fH-encoding nucleic acid sequence that has been humanized to comprise sequence encoding the human SCR6 domain can be introduced into the genome of the non-human animal such that it is expressed from the genome separately from the gene encoding endogenous fH polypeptide in the non-human animal host. One example of this is the transgenic mouse model, in which the engineered DNA encoding the sequence of interest is provided to a developing blastula and allowed to intercalate randomly into the DNA of the blastula cells. A second example of this is an animal in which the DNA has been provided by infection, for example, by adenoviral or lentiviral infection, which can be performed during embryonic development, postnatal development, or in the adult.

Alternatively, the engineered nucleic acid sequence can be introduced into the genome such that it is encoded by the genome from a specific locus, for example the locus of gene that is regulated in a desirable manner, for the purpose of restricting expression of the transgene or to replace an endogenous gene with the transgene, as in a "knock-in" transgenic animal. Such knock-in transgenic animals can be produced by introducing the engineered nucleic acid encoding the sequence of interest into embryonic stem (ES) cells, which are then screened to identify those in which the engineered DNA has "replaced" the endogenous sequence of the genome. The ES cells are then injected or otherwise mixed with the cells of a blastula so as to contribute to the developing animal. Typically, the nucleic acid that is introduced to generate such an animal is engineered such that the nucleic acid sequence will be regulated by the promoter of the gene it is replacing. As is well known in the art, in such cases, it is not necessary for the engineered nucleic acid sequence to comprise a complete non-human fH in which a sequence encoding human SCR6 has been swapped in to replace the non-human SCR6; instead, the non-human fH domains immediately flanking the SCR6 may be used.

Non-Human Animal Models Produced by fH Polypeptide Administration

The present disclosure also provides non-human animals that serve as models of Neisserial infection where the fH polypeptide (e.g., human fH polypeptide or other fH polypeptide having a human SCR6 amino acid sequence) is introduced into the bloodstream of the non-human animal from an exogenous source. For example, the fH polypeptide can be introduced by infusion into the bloodstream so as to provide for a level of fH polypeptide in the bloodstream that models that found in humans.

Methods of Use

The non-human animal models can be used in a variety of settings as exemplified below. In general, the non-human animal model can be used to test the efficacy of a candidate vaccine in eliciting bactericidal anti-Neisserial antibodies (e.g., anti-*Neisseria meningitidis* antibodies). Where the non-human animal model is infected either prior to or after administration of candidate agent, the models can find use in assessing the ability of a candidate agent (e.g., candidate antibiotic, candidate vaccine agent) to reduce bacterial load in the non-human animal.

In general, the non-human animal model is inoculated with a *Neisseria* (e.g., *Neisseria meningitidis* strain, *Neisseria gonorrhea* strain) of interest. Where the bacterium are taken from a culture (e.g., from a broth culture), the bacteria are usually washed prior to administration as described above. The inoculum can vary, e.g., from about $10^2$ to $10^9$ CFU/ml, about $10^4$ to $10^7$ CFU/ml, about $10^5$ to $10^6$ CFU/ml, and the like.

Screening Assays

Any of a variety of candidate agents can be screened by administration to the non-human animal models described herein. For example, the animal model can be used to identify candidate agents that, for example, inhibit or prevent infection by, replication of, or disease symptoms caused by a *Neisseria* (e.g., by *Neisseria meningitidis*).

"Candidate agents" is meant to include synthetic, naturally occurring, or recombinantly produced molecules (e.g., small molecule; drugs; peptides; antibodies (including antigen-binding antibody fragments, e.g., to provide for passive immunity) or other immunotherapeutic agents; endogenous factors present in eukaryotic or prokaryotic cells (e.g., polypeptides, plant extracts, and the like); etc.).

The non-human animal model described herein can be used to assess passive immunity provided by anti-Neisserial antibodies produced in a human or a non-human animal immunized with a Neisserial antigen. The non-human animal model described herein is also useful for testing passive protection against Neisserial strains expressing low levels of fHbp. For example, certain Neisserial strains such as, Group C strain 4243, can invade and replicate in the blood of infant rats (Welsch J A and Granoff D M, Infect Immun., 2004, 72 (10): 5903-9). These strains also survive in non-immune human serum and do not have detectable fH bound to them (Welsch J A, et al., J. Infect. Dis., 2008, 197 (7): 1053-61). Such strains tend to express low levels of fHbp. However, the fHbp of the low fHbp expressor strains is important for survival of the strain in human blood and human serum (Seib K L, Infect. Immun. 2009, 77 (1): 292-299). Thus, the non-human animal model is useful in assessing passive immunity even against the low expressors of fH.

Candidate agents encompass numerous types of molecules and numerous chemical classes, e.g., polypeptides, nucleic acids, organic molecules (e.g., small organic compounds having a molecular weight of more than 50 and less than about 2,500 daltons). Candidate agents can be obtained from a wide variety of sources including libraries of synthetic or natural compounds.

Screening of Candidate Anti-Neisserial Agents

The candidate agents can be assayed to assess, for example, the ability of the candidate agent to reduce bacterial load, facilitate anti-*Neisseria* antibody production, and the like. In general, the candidate agent is administered to the animal model, and the effects of the candidate agent assessed relative to a control (e.g., relative to an uninfected animal, relative to an infected animal treated with an agent having a known antibacterial effect, and the like). For example, the candidate agent can be administered to a *Neisseria meningitidis*-infected animal model and the bacterial titer of the treated animal compared to a bacterial titer of the animal prior to treatment and/or to a control, untreated animal. In general, a detectable and significant decrease in bacterial titer of an infected animal following treatment with a candidate agent is indicative of antibacterial activity of the agent.

The candidate agent can be administered in any manner desired and/or appropriate for delivery of the agent in order to affect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulations and routes. The agents can be administered singly or can be combined in combinations of two or more, especially where administration of a combination of agents may result in a synergistic effect.

The activity of the candidate agent can be assessed in a variety of ways. For example, where the host animal is infected with *Neisseria*, the effect of the agent can be assessed by examining serum samples for the presence of the pathogen (e.g., bacterial titer) or markers associated with the presence of the pathogen (e.g., a pathogen-specific protein or encoding nucleic acid, etc.) Qualitative and quantitative methods for detecting and assessing the presence and/or severity of bacterial infection are well known in the art. In one embodiment, the activity of an agent against Neisserial infection can be assessed by examining serum samples and/or tissue sections for the presence of bacteria.

As previously noted, the candidate agent may be a test serum from a human or a non-human animal immunized with a Neisserial antigen and the test serum may be assayed for its ability to confer passive immunity against *Neisseria* bacteria.

The test serum may be administered to the non-human animal model. A negative control serum, such as, serum from a non-immunized animal or serum obtained from the animal before immunization, may be administered to a non-human animal model as a negative control. The passive immunity conferred by the test serum may be assessed in a variety of ways as described above. Methods for assessing passive immunity against *Neisseria* bacteria are described by, for example, Welsch J A, et al., (J. Infect. Dis., 2003, 188 (11): 1730-40), Vu D M, et al., (J. Infect. Dis., 2006, 193 (6): 821-8).

Vaccine Development

The animal models disclosed herein can also be used to screen candidate vaccines for their ability to prevent or ameliorate infection by a Neisserial bacterium. In general, a "vaccine" is an agent that, following administration, facilitates the host in mounting an immune response against the target pathogen. The humoral, cellular, or humoral/cellular immune response elicited can facilitate inhibition of infection by the pathogen against which the vaccine is developed. Of particular interest are prophylactic vaccines that elicit a protective immune response that inhibits infection by and/or replication of *Neisseria* bacteria, e.g., *Neisseria meningitidis, N. gonorrhea*. Also of interest are therapeutic vaccines which provide protection against challenge, e.g., by production of bactericidal anti-Neisserial antibodies.

Screening of a candidate vaccine can be accomplished by, for example, administering the candidate agent prior to inoculation with a Neisserial bacteria. The candidate vaccine can be administered by a single bolus (e.g., intraperitoneal or intramuscular injection), which can be optionally followed by one or more booster immunizations. The induction of an immune response can be assessed by examining antibody responses, e.g., using conventional assays or the assay described herein. The immunized animal can be challenged with the *Neisseria*, and the immunized animals and, where desired non-immunized control animals, then observed for development of infection, and the severity of infection assessed (e.g., by assessing the titer of the *Neisseria* bacteria present.). Vaccine candidates that provide for a significant decrease in infection and/or significant increase in bactericidal anti-Neisserial antibodies are identified as viable vaccines.

EXAMPLES

The following example is provided to further illustrate the advantages and features of the present invention, but is not intended to limit the scope of the invention. While they are typical of those that might be used, other procedures, methodologies, or techniques known to those skilled in the art may alternatively be used.

Materials and Methods

Bacterial Strains.

*N. meningitidis* group C strain 4243 was used to measure bactericidal activity of immune human (vaccinee) sera using infant rabbit complement. This strain has been characterized previously (Harris, S. L. et al. (2003) *Infect Immun* 71:275-286; D. M. et al. (2005) *Vaccine* 23:4307-4314; Welsch, J. A. et al. (2004) *Infect Immun* 72:5903-5909; Granoff, D. M. et al. (2005) *Pediatr Infect Dis J* 24:132-136). The tested strains includes three Group B *N. meningitidis* strains, H44/76, Cu385 and NZ98/254 that have been used to prepare outer membrane vesicle (OMV) vaccines that have been shown to be efficacious in humans (Sierra, G. V. et al. (1991) *NIPH Ann* 14:195-207 and 208-110; Bjune, G. et al. (1991) *Lancet* 338: 1093-1096; Kelly, C. et al. (2007) *Am J Epidemiol* 166:817-823). Each strain also has been used extensively to measure meningococcal serum bactericidal antibody responses in vaccinated humans (Tappero, J. W. et al. (1999) *Jama* 281:1520-1527; Perkins, B. A. et al. (1998) *J Infect Dis* 177:683-691; M. et al. (1999) *Vaccine* 17:2377-2383; Wong, S. et al. (2007) *Pediatr Infect Dis J* 26:345-350; Wedege, E. et al. (2007) *Clin Vaccine Immunol* 14:830-838; Sandbu, S. et al. (2007) *Clin Vaccine Immunol* 14:1062-1069; Oster, P. et al. (2007) *Vaccine* 25:3075-3079; Thornton, V. et al. (2006) *Vaccine* 24:1395-1400). Survival of the three group B strains was tested in infant rat serum. Further, one of the three strains, H44/76, was chosen to investigate the survival of organisms in the bloodstream of infant rats upon the administration of human fH. In previous studies, this strain has been used in an infant rat bacteremia model to measure passive protective activity of antibodies elicited by OMV vaccines (Toropainen, M. et al. (1999) *Vaccine* 17:2677-2689; Toropainen, M. et al. (2005) *Vaccine* 23:4821-4833; Toropainen, M. et al. (2005) *Infect Immun* 73:4694-4703; Toropainen, M. et al. (2001) *Microb Pathog* 30:139-148).

The serotype (PorB), serosubtype (PorA) and sequence type (ST) of strain 4243 are 2a, P1.5,2 and ST-11, respectively, The corresponding classifications of strain H44/76 are 15, P1.7,16 and ST-32; strain Cu385 are 4,7 P1.19,15 and ST-33; and strain NZ98/254 are 4, P1.4 and ST-42. Strains H44/76 and Cu385 are high expressers of factor H binding protein (fHbp) in the variant 1 group and have amino acid sequences of fHbp that are identical to that of strain MC58 (Masignani, V. et al. (2003) *J Exp Med* 197:789-799). Strains 4243 and NZ98/254 express relatively lower amounts of subvariants of fHbp in the variant group 1 (<12 percent differences in amino acid identity with that of fHbp of strain MC58) (Welsch, J. A. et al. (2004) *J Immunol* 172:5606-5615; Welsch, J. A. et al. (2008) *J Infect Dis* 197:1053-1061).

Serum Samples.

Frozen sera obtained immediately before and one month after vaccination of children, aged 4- to 5-years, who were immunized with a quadrivalent meningococcal polysaccharide, or sera from adults immunized with a group C meningococcal oligosaccharide-$CRM_{197}$ conjugate vaccine were available from previous studies (King, W. J. et al. (1996) *J Pediatr* 128:196-202; Vu, D. M. et al. (2006) *Clin Vaccine Immunol* 13:605-610). In the present study, a convenience sample of sera from 69 children and 11 adults was selected based on availability of volumes of sera to perform the assays.

Binding of Primate fH to *N. meningitidis*.

Chimpanzee, rhesus macaque and baboon complement were obtained from a commercial supplier (Bioreclamation, Hicksville, N.Y.). Human serum (positive control for fH binding) was obtained from 10 healthy adult volunteers and pooled. All sera used in this assay were heated at 56° C. for 30 min to prevent complement activation and C3b binding to bacteria, which in turn could serve as an additional ligand for binding of fH. Binding of chimpanzee, rhesus macaque and baboon fH to strain H44/76 was measured by western blotting as described previously with *N. gonorrhoeae* using polyclonal anti-human fH (Bethyl Laboratories, NY) which also binds to fH from primates (Ngampasutadol, J. et al. (2008) *J Immunol* 180:3426-3435). After incubation of the bacteria with the respective sera, the bacteria were washed, solubilized, and the analyzed by SDS-PAGE. fH was detected by Western blot.

Inhibition of Binding of Human Factor H to *N. meningitidis* by Rat and Rabbit Serum.

Because only polyclonal anti-human fH was available as a means to measure direct fH binding to bacteria and the reagent does not cross-react with fH from non-primates such as rat or rabbit, binding of non-primate fH to *N. meningitidis* could not be directly addressed. Instead, the ability of rat or rabbit serum to inhibit binding of human fH to *N. meningitidis* was measured by flow cytometry. In brief, rat or rabbit and control human sera were heated at 56° C. for 30 min to prevent C3b binding to bacteria. Heat-inactivation of serum does not affect the complement inhibitory function or binding properties of fH (Jarva, H. et al. (2002) *J Immunol* 168:1886-1894; Ram, S. et al. (1998) *J Exp Med* 188:671-680).

*N. meningitidis* strain H44/76 was harvested from chocolate agar plates following 6-8 hours of growth and suspended in Hanks Basic Salt Solution (HBSS) containing 1 mM $CaCl_2$ and 1 mM $MgCl_2$ ($HBSS^{2+}$) to approximately $5 \times 10^7$ CFU/ml. The bacterial suspension was incubated with 40 µl of heat-inactivated human, rat or rabbit serum for 10 min at 37° C. in a reaction volume of 100 µl, followed by the addition of 5 µg of biotinylated human factor H (biotinylation was performed using NHS-LC-Biotin (Pierce) at a biotin:fH molar ratio of 20:1 according to the manufacturer's instructions). The reaction mixture (final volume 110 µl) was incubated for an additional 15 min, followed by detection of bound biotinylated human fH by flow cytometry using EXTRAVIDIN-FITC (Sigma) at a 1:100 dilution.

Heterologous C3 Deposition on *N. meningitidis* and Inhibitory Effect of Human fH.

The deposition of rat C3 on strains H44/76 and NZ98/254 that had been incubated with infant rat serum (final concentration of 10% (v/v)) was measured. Rat C3 that bound to bacteria was measured by flow cytometry (24) using FITC-conjugated anti-rat C3. Using flow cytometry, the ability of human fH to limit rat C3 deposition to strain H44/76 was assessed by increasing the concentrations (ranging from 0 to 50 µg/ml) of human fH added to infant rat serum, followed by incubation of the serum (final concentration of 20%) and fH mixtures with $5 \times 10^7$ bacteria. In some experiments, EGTA and $MgCl_2$ (both to a final concentration of 10 mM) were added to the rat serum to block the classical and lectin pathways of complement and selectively allow alternative pathway activation. As a control for the integrity of the alternative pathway of complement, zymosan was used, which is a potent activator of the alternative pathway of complement (Fearon, D. T. et al. (1977) *Proc Natl Acad Sci USA* 74:1683-1687). Zymosan (Sigma) was suspended in PBS to a concentration of 10 mg/ml. Ten µl of this suspension was added to infant rat serum that contained human fH as described above in a final reaction volume of 50 µl.

Survival of *N. meningitidis* in Infant Rat Serum.

Survival of *N. meningitidis* was tested in sera from 9 to 20 infant rats, depending on the strain. The sera were obtained by cardiac puncture from pups from 6 litters and had been stored at −70° to maintain endogenous complement. Bacteria for the assay were grown to log-phase in Mueller Hinton broth (BD, Franklin Lakes, N.J.) supplemented with 0.25% glucose (wt/vol) and 0.02 mM cytidine-5'-monophospho-N-acetyl-neuraminic acid (Sigma-Aldrich Co., St. Louis, Mo.) for approximately 2 hrs (to $A_{620\ nm}$ of ~0.6). The bacteria were washed as described elsewhere (52) and resuspended in Dulbecco's phosphate buffered saline (DPBS, Mediatech, Herndon, Va.) containing 0.9 mM $Ca^{2+}$ ($CaCl_2 \times 2\ H_2O$) and 0.5 mM $Mg^{2+}$ ($MgCl_2 \times 6\ H_2O$) and 1% (wt/vol) bovine serum albumin (BSA Cohn Fraction V, Equitech-Bio, Inc., Kerrville, Tex.) ($DPBS/Ca^{2+}/Mg^{2+}$-1% BSA). The final 40 µl reaction mixture contained about 400 CFU of bacteria, 20%, 40% or 60% serum, and 0 or 50 µg/ml of purified human fH (Complement Technologies, Inc., Tyler, Tex.). Percent survival of the bacteria in each reaction mixture was determined by comparison of the respective CFU/ml present after 60 min incubation with those at time 0 in the negative control reactions. The negative control contained bacteria and 20 or 40% serum from a non-immune adult human with no endogenous bactericidal activity against any of the strains tested and typically resulted in greater than 150% survival after 60 min incubation at 37° C.

Complement-Mediated Serum Bactericidal Activity.

Group C bactericidal titers were measured against log-phase, washed organisms that had been grown washed and resuspended in $DPBS/Ca^{2+}/Mg^{2+}$-1% BSA as described above for performing the survival of *N. meningitidis* in infant rat serum. The complement source was 20 percent pooled infant rabbit serum instead of non-immune human serum. The rabbit serum pool (Pel-Freeze, Rogers, Ark.) showed no detectable bactericidal activity (the CFU/ml of the test strain in 20 or 40 percent serum increased by more than 150 percent during a 1 hr incubation, as compared with CFU/ml at time 0).

Bacteremia in Infant Rats.

Pregnant out-bred Wistar rats (Charles River, Portage, Mich.) were obtained, and 4-6 days after birth, the pups were randomly redistributed to the nursing mothers to prevent maternal bias in the different treatments of the experiment. Animal experiments were conducted using protocols approved by the CHORI IACUC. Bacteria were grown and washed as described above for the serum bactericidal assay and resuspended in $DPBS/Ca^{2+}/Mg^{2+}$ containing 10% pooled heat-inactivated infant rat serum that had been passed over a 1 mL HiTrap Protein G HP column (GE Healthcare, Piscataway, N.J.) to remove IgG. By ELISA, there was no detectable IgG in the depleted sera (greater than 99% of the IgG was removed), and no detectable bactericidal activity in the sera before heat-inactivation.

The bacterial suspension was divided into five aliquots and placed in tubes. To three aliquots, purified human fH (Complement Technologies, Inc.) was added to achieve concentrations of 20 µg/ml, 100 µg/ml or 500 µg/ml (to deliver 2 µg, 10 µg or 50 µg/rat in the 100 µl used for the challenge). To a fourth aliquot, purified human C1 esterase inhibitor (Complement Technologies, Inc.) was added (500 µg/ml) as a negative control. A fifth aliquot with bacteria alone served as an additional negative control (0 µg of fH or C1 esterase inhibitor). At time 0, the pups were challenged IP with 100 µl containing washed, log-phase *N. meningitidis* (~$7 \times 10^3$ CFU/rat) together with doses of 0, 2, 10 or 50 µg human fH or 50 µg C1 esterase inhibitor. Eight hours after the bacterial challenge, blood specimens were obtained by cardiac puncture and aliquots of 1 µL, 10 µL and 100 µL of blood were plated onto chocolate agar (Remel, Lenexa, Kans.). The CFU/mL of blood was determined after overnight incubation of the plates at 37° C. in 5% $CO_2$.

Statistical Analysis.

The respective geometric means of CFU/ml at time 60 min were computed by exponentiating. When performing the $log_{10}$ transformations, samples below the lower limits of detection of bacteria were assigned a value of half of the lower limit (i.e. 5 CFU/ml). The significance of the respective differences in geometric means of the CFU/ml across the four groups given 50 µg, 10 µg, 2 µg or 0 µg of fH/rat was determined by one-way ANOVA. The significance of the differences in geometric means of CFU/ml obtained from animals treated with 50 µg of human fH vs. 50 µg of human C1 esterase inhibitor was determined by a T test.

Generation of fH Transgenic Cassette.

The human factor H gene (cfH) was amplified using plasmid with cfH (pBluescript-cfH; Ngampasutadol J., et al., J. Immunol. 180: 3426-35, 2008) as template. The amplified PCR product was cloned into the EcoRI restriction site of vector pCAGGS (pCAGGS contains chicken β-actin promoter: Niwa, H., K., et al., Gene 108:193-9, 1991). The resulting vector pCAGGS-cfH was digested with SalI and PstI and the approximately 6 kb transgenic cassette containing the promoter and the cfH gene was gel-purified. The purified cassette was used for microinjection of Wistar rat embryos.

Example 1

Species Specificity of Primate fH Binding to *N. Meningitidis*

Polyclonal anti-human fH recognized fH in heat-inactivated sera from humans as well as non-human primates (FIG. 1, Panel A, lanes marked 'serum alone') and can therefore be used to test primate fH binding to the bacteria. Binding of fH to strain H44/76 in heat-inactivated primate serum is shown in the lanes marked 'serum+bacteria'. Heat treatment did not affect the binding properties of fH (Jarva, H. et al. (2002) *J Immunol* 168:1886-1894; Ram, S. et al. (1998) *J Exp Med* 188:671-680). Bacteria incubated with human serum (positive control) showed the most fH binding, whereas binding of fH in chimpanzee serum was low, and binding was not detected with baboon and rhesus macaque sera.

Example 2

Rat or Rabbit fH Does Not Compete with Human fH for Binding to *N. Meningtidis*

An indirect flow cytometric assay was used to determine whether heat-inactivated rat or rabbit fH (in their respective heat-inactivated sera) competed with biotinylated human fH for binding to the same ligand on live *N. meningitidis*. The addition of 40 percent heat-inactivated rat or rabbit serum (the highest concentration tested) did not inhibit binding of biotinylated human fH to *N. meningitidis* whereas the addition of 40 percent heat-inactivated human serum, the positive control, inhibited binding of biotinylated human fH (FIG. 1, Panels B and C). These data indicate that rat and rabbit fH do not bind to the same ligand on *N. meningitidis* as human fH. Although the possibility that rat and rabbit fH may bind to sites on meningococci distinct from sites that bind human fH cannot be excluded, an alignment of the amino acid sequences of human fH, rhesus macaque fH, and rat fH, (derived from the NCBI database) showed that human and rhesus fH bears about 88% amino acid sequence identity, compared to about 64% amino acid sequence identity between human and rat fH. Because rhesus fH did not bind to meningococci (FIG. 1, Panel A), the lack of inhibition of human fH by rat or rabbit serum was consistent with fH from these species also not binding to meningococci.

Example 3

Effect of Human fH Added to Infant Rat Serum on Survival of *N. Meningitidis*

Figure 2:
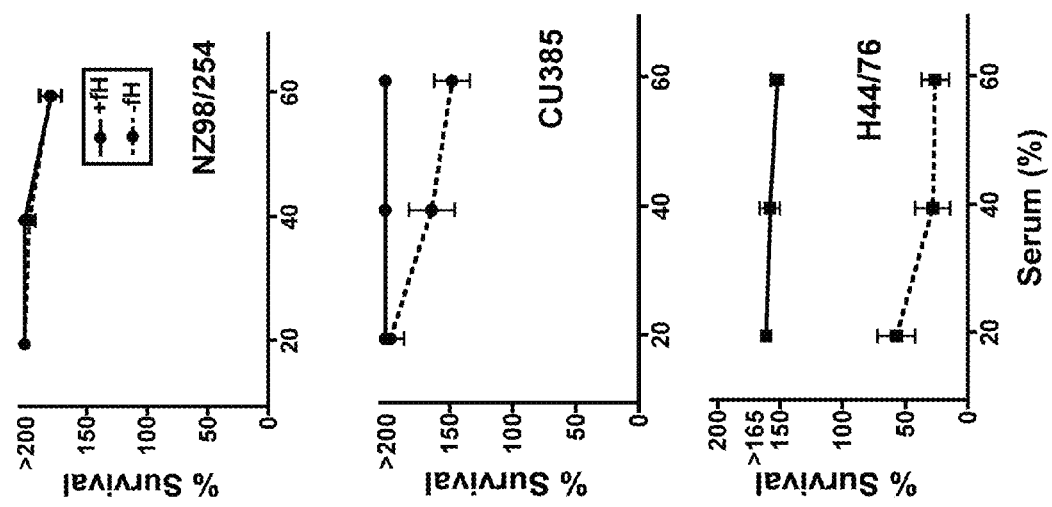
FIG. 2 depicts the effect of addition of human fH on survival of Neisseria meningitidis in infant rat serum. Bacteria (~10,000 CFU/ml) were suspended in different concentrations of infant rat sera. Each serum was divided into two aliquots to which 50 μg/ml or 0 μg/ml of human fH was added. The sera and bacteria were incubated for 1 hr at 37° C. Dotted lines, percent survival of bacteria in sera without added fH; solid lines, percent survival in sera with human fH. Data are mean±95% confidence intervals of results from 9 to 20 sera per strain.

The effect of adding human fH to infant rat serum upon the survival of three strains of *N. meningitidis* was measured when they were incubated in the mixture for 1 hr at 37° C. (FIG. 2). Each of the sera was tested at concentrations of 20, 40 and 60 percent. In the absence of added fH, survival of two of the strains, NZ98/254 and Cu385 (upper and middle panels of FIG. 2, respectively), increased by more than 150 percent during the incubation period compared with the respective survival at time 0. In contrast, survival of the third strain, H44/76, decreased by 40 to 60 percent in all three serum concentrations (lower panel). When human fH was added at a concentration of 50 µg/ml to the reaction, the corresponding survival of strain H44/76 increased by >150 percent (for example, 152% survival in 60% sera containing human fH, as compared with 26% survival in the absence of added human fH, P<0.001). Survival of one of the two already serum-resistant strains (strain NZ98/254) was not affected by the addition of human fH while survival of the second serum-resistant strain, Cu385, increased further in 40% and 60% serum (fH, P<0.001).

The importance of the presence of physiologically relevant levels of human fH to the survival of strain H44/76 in serum is underscored by the observation that although strain H44/76 showed poor survival in infant rat serum in the absence of added human fH, this strain survived when incubated in human serum from an adult who lacked naturally-acquired bactericidal antibodies (>130 percent survival at 1 hr at 37° C. in 20, 40 or 60 percent sera, data not shown). These results are similar to those of our previous study showing survival and growth of strain H44/76 incubated with anticoagulated whole human blood or plasma from a healthy adult who lacked meningococcal bactericidal or opsonic antibodies (Welsch, J. A. et al. (2008) *J Infect Dis* 197:1053-1061).

Example 4

Binding of Rat C3 to Meningococci and Its Regulation by Human fH

Figure 3:
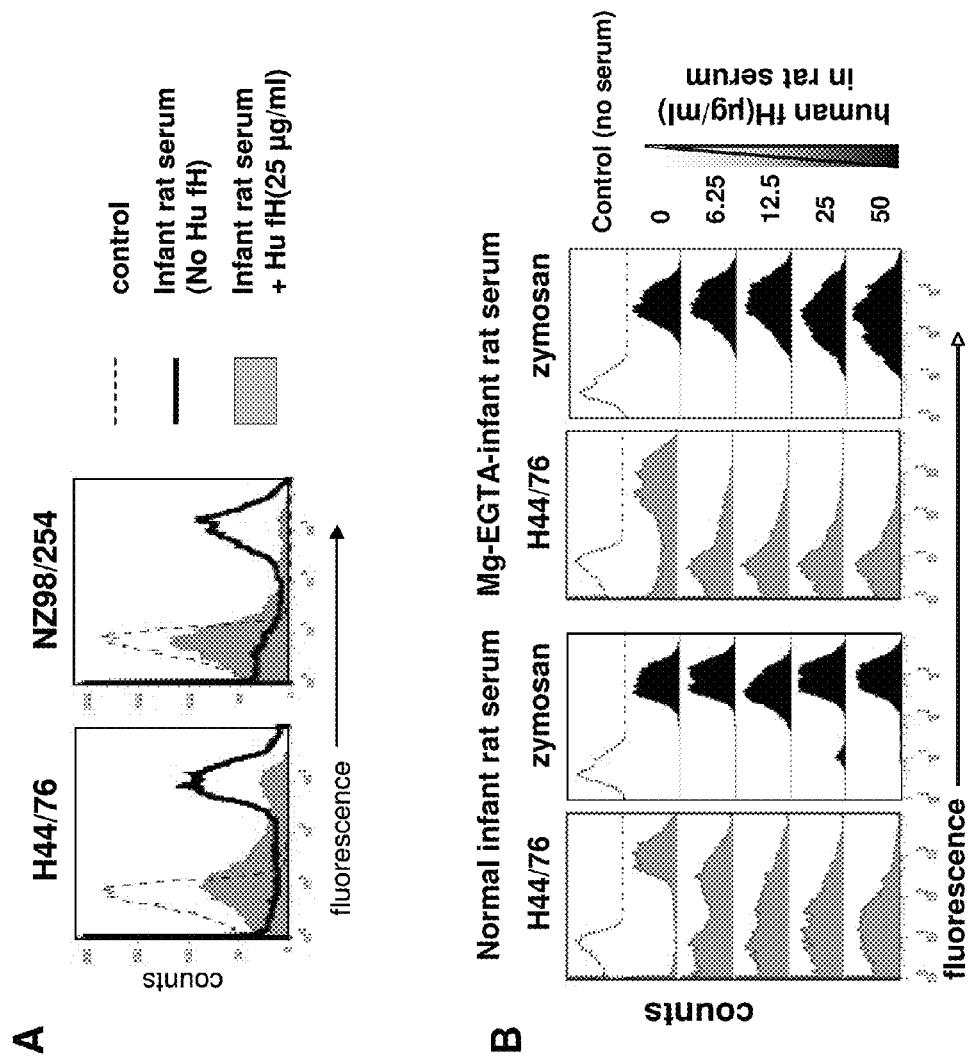
FIG. 3, Panels A and B depicts the binding of rat C3 to N. meningitidis and regulation of rat C3 binding by human fH (Hu fH). (Panel A) Rat C3 binding to strains H44/76 and NZ98/254 incubated with infant rat complement without added human fH (solid line) or that contained 25 μg/ml human fH (shaded grey histograms). (Panel B) Concentration-dependent inhibition of rat C3 binding by human fH. Bacteria were incubated with 10% infant rat serum alone, or 10% rat serum to which human fH was added at concentrations ranging from 50 to 6.25 μg/ml. C3 deposition on bacteria was measured by flow cytometry using anti-rat C3-FITC. Binding of rat C3 to zymosan, an alternative pathway activator, was measured under similar conditions as a control. The x-axis represents fluorescence on a $log_{10}$ scale and the y-axis the number of events. (Panel C) Human fH binding to bacteria regulates rabbit alternative pathway activation. Dose responsive inhibition by Hu fH of rabbit C3 binding to meningococci. Strain A2594 was incubated with Mg/EGTA-treated baby rabbit complement that contained Hu fH at doses ranging from 0 to 64 μg/ml (left graph) and rabbit C3 bound to bacteria was measured by flow cytometry. Zymosan, an activator of the alternative pathway, was used as a control (right graph) to ensure that inhibition of rabbit C3 binding was not the result of nonspecific complement inhibition. Control histograms (no serum added) are indicated by the broken lines.

To investigate the basis for differences in resistance to killing by infant rat serum among strains, binding of rat C3 to strains H44/76 (sensitive to killing by infant rat serum) and NZ98/254 (resistant to killing) was measured. When incubated in infant rat serum, strains NZ98/254 and H44/76 bound similar amounts of rat C3 (FIG. 3, Panel A, histograms depicted by solid lines). Thus, regulation at or prior to C3 deposition (as determined by total C3 binding) did not account for resistance of NZ98/254 and susceptibility of H44/76 to bactericidal activity of infant rat serum. Addition of 25 µg/ml of human fH was added to the rat complement resulted in decreased rat C3 binding to both strains (FIG. 3, Panel A, shaded grey histograms). The efficiency of rat C3 regulation on strain H44/76 by human fH was determined so as to assess a possible correlation with diminished sensitivity to killing by rat serum. The addition of human fH decreased rat C3 binding to H44/76 in a dose responsive fashion (FIG. 3, Panel B); almost complete inhibition was seen when 25 and 50 µg/ml of human fH was added to rat serum while partial inhibition was seen at a human fH concentration of 6.25 µg/ml in rat serum. Experiments that employed the alternative pathway of complement exclusively (Mg-EGTA added to rat serum supplemented with human factor H to block the classical pathway of complement) demonstrated enhanced efficiency of C3 regulation (diminished C3 binding) when the classical pathway was absent. FIG. 3, Panel C shows that human fH binding to bacteria also regulates rabbit alternative pathway activation in a dose-dependent manner.

To ensure that inhibition of rat C3 binding to strain H44/76 did not result from nonspecific inhibition of complement activation, parallel experiments using zymosan, a potent activator of the alternative pathway of complement (Fearon, D. T. et al. (1977) *Proc Natl Acad Sci USA* 74:1683-1687) were performed. Alternative pathway specific complement activation and rat C3 binding to zymosan occurred in an uninhibited manner in rat serum supplemented with increasing concentrations of human fH (some inhibition was seen at higher concentrations of fH; experiments not shown).

Example 5

Effect of Human fH on Meningococcal Bacteremia in Infant Rats

Figure 4:
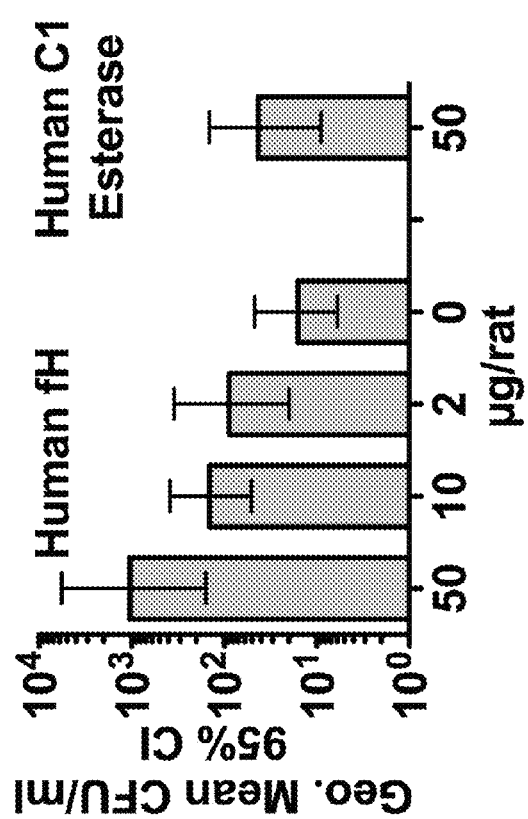
FIG. 4 depicts the effect of co-administration of human fH on bacteremia after IP challenge of infant rats with group B strain H44/76. Each group consisted of 15 rats per group except for animals given 0 μg of fH where the number of animals was 10. Bacteremia was measured in blood cultures obtained 8 hours after bacterial challenge. Rats treated with 50 μg of human fH had a higher geometric mean CFU/ml than controls treated with 50 μg of human C1 esterase inhibitor ($P<0.005$). The respective geometric means of the four groups given 50, 10, 2 or 0 μg/rat of human fH was significant ($P<0.02$ by ANOVA).

To determine whether human fH enhanced survival of *N. meningitidis* in vivo, doses of 2, 10 or 50 µg of human fH were co-administered to infant rats (N=15/group) challenged with about $7 \times 10^3$ log-phase CFU of strain H44/76 per rat. As negative controls one group of rats was given the bacterial challenge without human fH (0 µg) and a second group with 50 µg per rat of human C1 esterase inhibitor. Blood cultures were obtained 8 hrs after the challenge. Diminishing numbers of bacteria (CFU/ml) were isolated from the blood of animals that had been administered decreasing (50, 10, 2 or 0 µg) amounts of fH mixed with the infecting inocula (FIG. 4, P<0.02 by ANOVA). The geometric mean CFU/ml isolated from the blood of animals given the highest human fH dose tested, 50 µg, was significantly higher than CFU/ml isolated from controls given 50 µg of human C1 esterase inhibitor (1050 vs. 43, P<0.005, T-test).

Example 6

Effect of Human fH on Immune Human Serum Bactericidal Titers Elicited by Baby Rabbit Complement Group C bactericidal titers were measured using rabbit complement in pre- and 1-month post-immunization sera from 69 children, aged 4-5 years who were immunized with meningococcal polysaccharide vaccine. Nineteen children had titers <1:16 in pre-immunization sera (the lowest dilution tested) and titers of 1:64 or greater in post-immunization sera.

Figure 5:
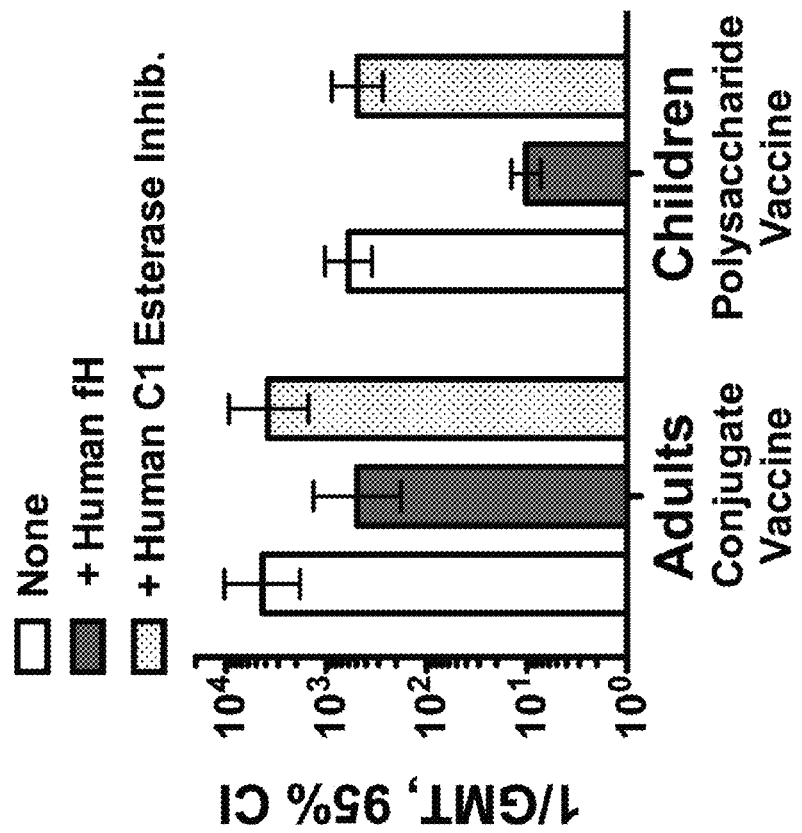
FIG. 5 depicts the effect of addition of human fH (25 μg/ml) on serum group C serum bactericidal titers measured with infant rabbit complement. The sera were obtained from 11 adults one month after immunization with a group C meningococcal conjugate vaccine or 19 children, aged 4 years, one month after immunization with quadrivalent meningococcal polysaccharide vaccine.
Figure 6:
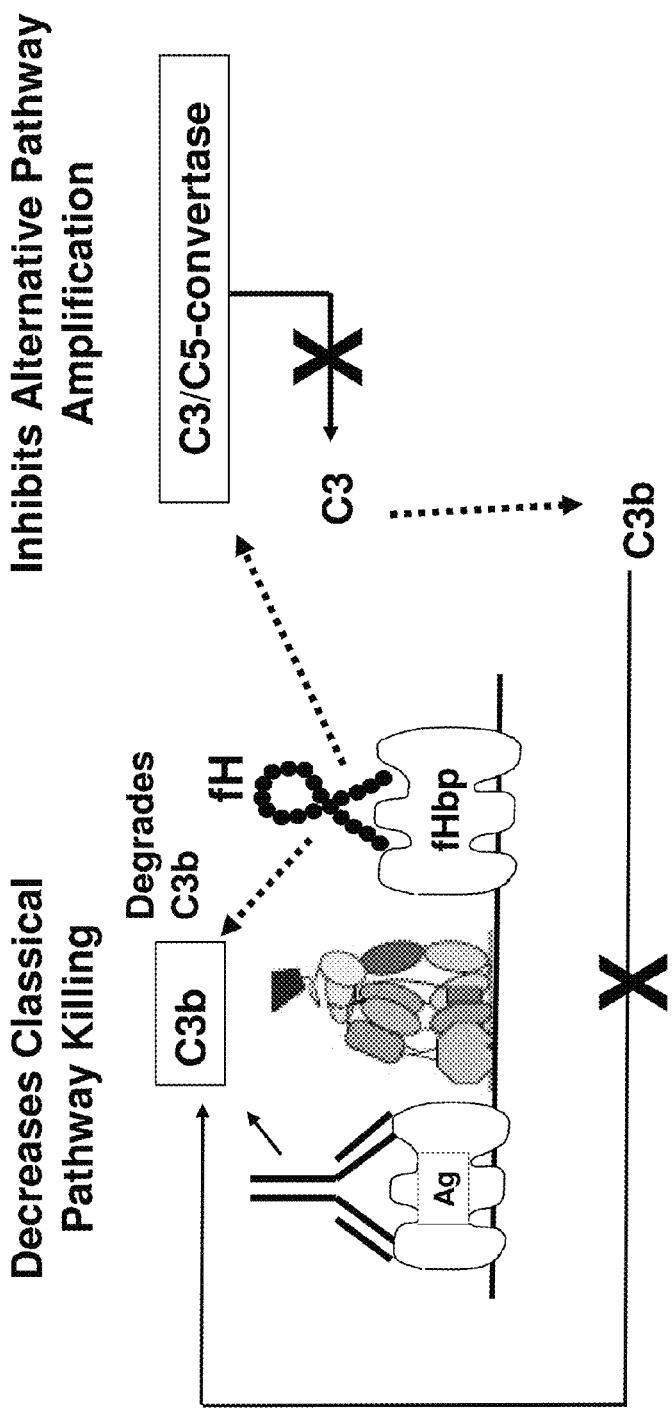
FIG. 6 depicts the effect of fH binding on N. meningitidis resistance to complement-mediated killing.

The titers of the 19 positive post-immunization sera were re-assayed with rabbit complement alone, rabbit complement with 25 µg/ml human fH added, or as a control, 25 µg/ml of human complement C1 esterase inhibitor. Similar assays were performed on post-immunization sera from 11 adults immunized with a group C meningococcal conjugate vaccine. The results are summarized in FIG. 5. When human fH was added to the reactions, the serum bactericidal geometric mean titer (GMT) of adults decreased more than 8-fold (P<0.001) and that of the children decreased by 60-fold (P<0.001). When human C1 esterase inhibitor was added, the respective GMTs were not significantly different from the respective titers measured without the inhibitor (P>0.5).

Example 7

Generation of F0 Transgenic Rats Expressing Human fH

Figure 8:
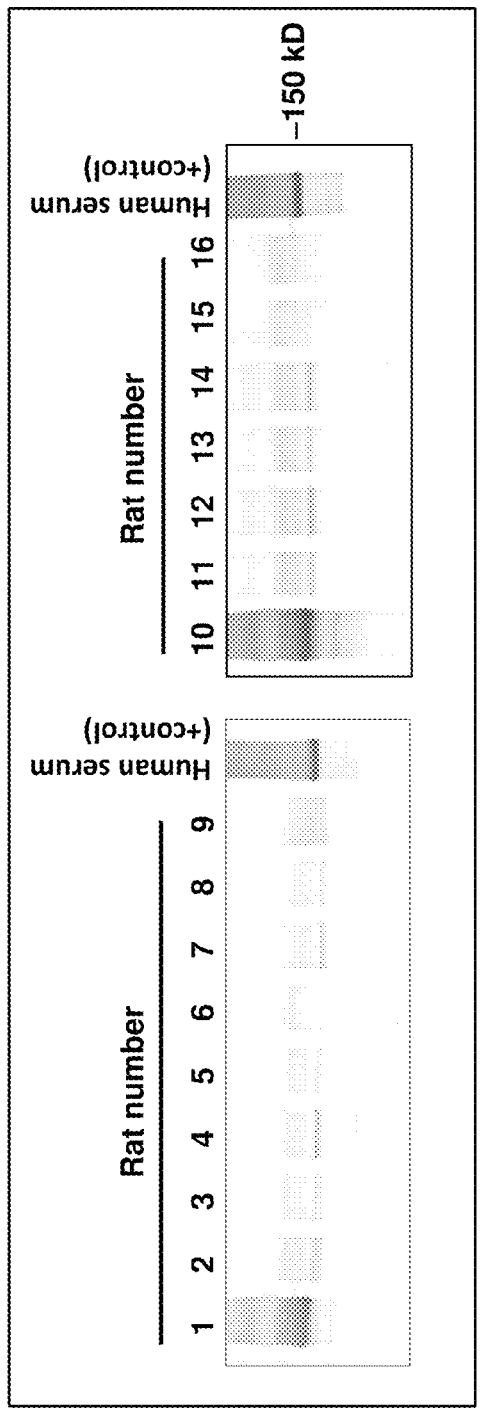

Rat embryos were injected with purified human fH transgenic cassette (see materials and methods). Microinjected rat embryos were implanted into pseudopregnant female Wistar rats. Screening of F0 generation litter for expression of human fH in serum was performed by western blotting using affinity-isolated polyclonal goat anti-human fH (Granoff, D. M., J. A. Welsch, and S. Ram. 2009. Infect Immun 77:764-9; Ngampasutadol J., et al., J. Immunol. 180: 3426-35, 2008). Lanes were loaded with 0.5 µl serum from 16 F0 rat pups. 0.06 µl human serum was used as positive control. Two of 16 animals (F0 generation) expressed human fH in their serum (FIG. 8).

Example 8

Generation of Transgenic Rats Expressing Human fH

F0 transgenic rats expressing fH are mated with wild-type Wistar rats and pups from this mating (F1 generation) and are screened for fH expression in serum as described in Example 7. The presence of the cfH gene in these pups is determined by PCR. Rats from the F1 generation that express human fH are identified as having human cfH integrated into germ-line cells and are used for further breeding to generate homozygous transgenic rats expressing human fH.

Dicussion

The above demonstrates that (a) binding of fH to *N. meningitidis* is specific for human fH, (b) the addition of human fH to infant rat serum increased resistance of the bacteria to complement-mediated bactericidal activity and decreased rat C3 deposition, and (c) administration of human fH to infant rats at the time of intraperitoneal challenge with group B *N. meningitidis* increased survival of organisms by more than 1 $\log_{10}$. Further, group C bactericidal titers measured in sera of immunized children and adults using infant rabbit complement decreased 8- to 60-fold when human factor H was added to the test reaction mixtures.

The important role of complement in host defense against *N. meningitidis* was first reported nearly 30 years ago (Nicholson, A. et al. (1979) *Science* 205:298-299). Twenty-five years ago Zollinger and Mandrell reported that serum bactericidal titers measured with rabbit complement were much higher than the respective titers measured with human complement (Zollinger, W. D. et al. (1983) *Infect Immun* 40:257-264), an observation confirmed by subsequent studies (Santos, G. F. et al. (2001) *Clin Diagn Lab Immunol* 8:616-623). The data above (FIG. 5) showed that the addition of human fH decreased the bactericidal titers measured in sera from immunized children or adults using rabbit complement. Thus, the ability of meningococci to selectively bind to human fH may be one reason for the higher bactericidal titers measured with nonhuman complement sources. Note that at the high dilutions of human sera tested in our study ($\geq 1:64$), human fH would be expected to be limited. However, at lower dilutions of human serum, concentrations of human fH would be expected to be sufficient to down-regulate rabbit C3, which may contribute to the occasional observed "prozone" with rabbit complement (i.e., lack of bactericidal activity at low dilutions of human test sera but the presence of bactericidal activity at high dilutions when rabbit C3 activation is no longer down-regulated by human fH).

What is claimed is:

1. A method of detection of bactericidal antibodies specific to *Neisseria meningitidis* in a biological sample, the method comprising:
    combining in a reaction mixture:
    viable *Neisseria meningitidis* expressing a surface factor H binding protein (fHbp);

a biological sample from a human suspected of containing bactericidal antibodies specific to *Neisseria meningitidis,* a substantially purified factor H (fH) polypeptide comprising the amino acid sequence of a human Short Consensus Repeat 6 (SCR 6); and a complement of a non-human animal having no detectable anti-*Neisseria meningitidis* bactericidal activity; and detecting the presence or the absence of the bactericidal antibodies specific to the *Neisseria meningitidis* in the sample by assessing viability of the *Neisseria meningitidis*, wherein decreased viability of the *Neisseria meningitidis* in the presence of the sample indicates that the sample contains the bactericidal antibodies specific to the *Neisseria meningitidis*.

2. The method of claim 1, wherein the bactericidal antibodies specific to the *Neisseria meningitidis* in the biological sample are antibodies to the capsular polysaccharide of the *Neisseria meningitidis* and the biological sample is human serum.

3. The method of claim 1, wherein the substantially purified fH polypeptide is a human fH polypeptide.

4. The method of claim 1, wherein the substantially purified fH polypeptide is a chimeric fH polypeptide comprising the amino acid sequence of an fH polypeptide endogenous to the non-human animal modified to contain the amino acid sequence of the human SCR6.

5. The method of claim 1, wherein the non-human complement is rabbit complement.

6. The method of claim 1, wherein the non-human complement is rat complement or mouse complement.

7. The method of claim 1, wherein the *Neisseria meningitidis* is a Group A, B, C, X, Y or W-135 *Neisseria meningitidis*.

8. The method of claim 1, wherein the sample is human serum.

9. The method of claim 1, wherein the substantially purified fH polypeptide is added to the reaction mixture in an amount of 5 µg/ml or more.

10. The method of claim 1, wherein the substantially purified fH polypeptide is added to the reaction mixture in an amount of 10 µg/ml or more.

11. The method of claim 1, wherein the substantially purified fH polypeptide is added to the reaction mixture in an amount of 20 µg/ml or more.

12. The method of claim 1, wherein the substantially purified fH polypeptide is added to the reaction mixture in an amount of 50 µg/ml or more.

13. The method of claim 3, wherein the substantially purified fH polypeptide is added to the reaction mixture in an amount of 5 µg/ml or more.

14. The method of claim 3, wherein the substantially purified fH polypeptide is added to the reaction mixture in an amount of 10 µg/ml or more.

15. The method of claim 3, wherein the substantially purified fH polypeptide is added to the reaction mixture in an amount of 20 µg/ml or more.

16. The method of claim 3, wherein the substantially purified fH polypeptide is added to the reaction mixture in an amount of 50 µg/ml or more.

17. The method of claim 5, wherein the substantially purified fH polypeptide is added to the reaction mixture in an amount of 5 µg/ml or more.

18. The method of claim 5, wherein the substantially purified fH polypeptide is added to the reaction mixture in an amount of 10 µg/ml or more.

19. The method of claim 5, wherein the substantially purified fH polypeptide is added to the reaction mixture in an amount of 20 µg/ml or more.

20. The method of claim 5, wherein the substantially purified fH polypeptide is added to the reaction mixture in an amount of 50 µg/ml or more.

* * * * *